US007496550B2

(12) United States Patent
Rice et al.

(10) Patent No.: US 7,496,550 B2
(45) Date of Patent: Feb. 24, 2009

(54) TECHNIQUES FOR RECONSTRUCTING SYNTHETIC NETWORKS USING PAIR-WISE CORRELATION ANALYSIS

(75) Inventors: J. Jeremy Rice, Mohegan Lake, NY (US); Gustavo Stolovitzky, Riverdale, NY (US); Yuhai Tu, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 1384 days.

(21) Appl. No.: 10/699,283

(22) Filed: Oct. 31, 2003

(65) Prior Publication Data

US 2005/0096887 A1 May 5, 2005

(51) Int. Cl.
  G06F 17/00 (2006.01)
  G06N 5/02 (2006.01)
(52) U.S. Cl. .............................. 706/47; 706/12; 706/14
(58) Field of Classification Search ................ 706/47, 706/12, 1
  See application file for complete search history.

(56) References Cited

OTHER PUBLICATIONS

V. Anne Smith et al., Evaluating functional network inference using simulations of complex biological systems, Jul. 2002, Oxford University Press, S216-S224.*
H. Jeong, The large-scale organization of metabolic networks, Oct. 2000, Nature, vol. 407, 651-653.*
V. Anne Smith et al., Influence of Network Topology and Data Collection on Network Inference, Duke University, No date provided.*
John R. Koza et al., Reverse Engineering of Metabolic Pathways from Observed Data Using Genetic Programming, No Date Provided, Stanford University.*
Jeong et al., "The Large-Scale Organization of Metabolic Networks," Nature, vol. 407, pp. 651-654 (Oct. 5, 2000).
Jeong et al., "Lethality and Centrality in Protein Networks," Nature, vol. 411, pp. 41-42 ( May 3, 2001).
Koza et al., "Reverse Engineering of Metabolic Pathways from Observed Data Using Genetic Programming.", no date.
Milo et al., "Network Motifs: Simple Building Blocks of Complex Networks," Science, vol. 298, pp. 824-827 (Oct. 25, 2002).
Samoilov et al., "On the Deduction of Chemical Reaction Pathways from Measurements of Time Series of Concentrations," Chaos, vol. 11, No. 1, pp. 108-114 (Mar. 2001).
Shen-Orr et al., "Network Motifs in the Transcriptional Regulation Network of *Escherichia coli*," Nature Genetics (Apr. 22, 2002).
Smith et al., "Influence of Network Topology and Data Collection on Network Inference.", no date.
Strogatz, S.H., "Exploring Complex Networks," Nature, vol. 410, pp. 268-276 (Mar. 8, 2001).

(Continued)

*Primary Examiner*—Joseph P Hirl
(74) *Attorney, Agent, or Firm*—Ryan, Mason & Lewis, LLP

(57) ABSTRACT

Techniques for reconstructing networks are provided. In one aspect, a method for reconstructing a synthetic network, such as a synthetic biological network, is provided. In another aspect, a method for reconstructing a supply chain network is provided. Exemplary supply chain networks include supply chains for petroleum distribution.

29 Claims, 12 Drawing Sheets

OTHER PUBLICATIONS

Uetz et al., "A Comprehensive Analysis of Protein-Protein Interactions in *Saccharomyces cerevisiae*," Nature, vol. 403, pp. 623-627 (Feb. 10, 2000).

Woolf et al., "A Fuzzy Logic Approach to Analyzing Gene Expression Data," Physiol Genomics, vol. 3, pp. 9-15 (2000).

Yeung et al., "Reverse Engineering Gene Networks Using Singular Value Decomposition and Robust Regression," PNAS, vol. 99, No. 9 pp. 6163-6168 (Apr. 30, 2002).

* cited by examiner

EXAMPLE SUPPLY CHAIN FOR PETROLEUM

EXAMPLE OF RECONSTRUCTION USING PAIR-WISE CORRELATION INFERENCE

TECHNIQUES FOR RECONSTRUCTING SYNTHETIC NETWORKS USING PAIR-WISE CORRELATION ANALYSIS

CROSS REFERENCE TO RELATED APPLICATIONS

This application is related to U.S. Patent Application Number 20050096958, entitled TECHNIQUES FOR RECONSTRUCTING SUPPLY CHAIN NETWORKS USING PAIR-WISE CORRELATION ANALYSIS, filed concurrently herewith.

FIELD OF THE INVENTION

The present invention relates to network reconstruction and, more particularly, to techniques for reconstructing synthetic networks.

BACKGROUND OF THE INVENTION

Network reconstruction has become an important focus of current research as it impacts many areas of current consideration, such as supply chains, social networks, food chains and biological systems, such as metabolic and gene regulatory networks. For example, companies that manufacture goods will depend on a supply chain for both raw materials and subcomponents of the final manufactured product (or perhaps service). The network of suppliers may be a guarded secret of the company and not readily apparent to an outside observer. However, it may be desirable to be able to determine the network of suppliers.

Regarding biological systems, a fundamental task has been to try to understand how networks of genes interact to bring about cellular function. Pursuing this task requires both an understanding of the biology of the individual genes and gene products, as well as an understanding of the properties of complex networks. For an example illustrating the complexities of network theory, see S. H. Strogatz, *Exploring Complex Networks*, 410 NATURE 268-76 (2001).

The topic of reverse engineering chemical and biological networks based on protein to protein interactions, medical literature or time-series data from chemical reaction or gene expression experiments has been a subject of recent study. These efforts have sought to reconstruct network connectivity, and in some cases the kinetic relations, of the system under study. Four hierarchical levels of reverse engineering can be defined.

Topology is a level of reverse engineering concerned with identifying which nodes interact in the system, the goal being to map or diagram non-directional connections between all interacting nodes. Some examples of methods at this level include literature-based networks and protein to protein interaction maps based on yeast two-hybrid studies.

Topology and causality is a level of reverse engineering encompassing topology, and further encompassing the directionality of the interactions. The goal of this level is to map or diagram the directionality between all directly interacting variables. An example of a method at this level includes mutual information-based reconstructions of mitochondrial metabolic reactions.

Qualitative connections is a level of reverse engineering encompassing topology and causality and also providing a qualitative description of the interactions. More specifically, this method seeks to know all variables that can modify an output variable with a qualitative indicator of how the output will change, i.e., positively or negatively. Some examples of methods at this level include fuzzy logic analysis of facilitator/repressor groups in the yeast cell cycle and a Jacobian matrix elements method for chemical reactions.

Quantitative connections is a level of reverse engineering encompassing qualitative connections and also providing a quantitative description of the interactions. More specifically, for any given variable, this method seeks to know the mathematical relationship that maps its output as a function of the input. The goal of this level of reverse engineering is a set of equations that could simulate and reproduce the behavior of the actual system. Some examples of methods at this level include linear models of gene regulation and genetic algorithms for reconstructing synthetic data generated from E-cells, an in silico representation of an *Escherichia coli* cell.

At the qualitative connections level, methods for deducing chemical kinetic systems are described in M. Samoilov et al., *On the Deduction of Chemical Reaction Pathways From Measurements of Time Series of Communications*, 11 CHAOS 108-114 (2001). In these methods, some inputs are affected while mutual information is computed between all pairs of reactant concentrations, i.e., the nodes in the network. These methods attempt to determine the whole reaction scheme, or map, by considering which nodes are "closer" or "farther" to each other in a metric-type space, determined by correlating the nodes.

A potential difficulty may arise in such methods when all reactant concentrations cannot be determined to the same degree of accuracy. Thus, an encompassing, global reconstruction may not be feasible when one cannot obtain accurate data for all nodes. Moreover, with such methods the input signal must result in the perturbation of all the nodes such that the correlations reveal the unknown connections between the nodes. The methods, however, do not provide for determining such an input signal for arbitrary (random) and/or hidden networks.

Another common method of reconstructing biological networks is a Bayesian inference approach, such as that used to analyze gene expression data. See Friedman et al., *Using Bayesian Networks to Analyze Expression Data*, 7 J. COMPUT. BIOL. 601-620 (2000). The Bayesian inference approach attempts to construct a model that can "explain" data based on conditional probabilities between upstream nodes called "parents" and their dependent "child" nodes. The complete dependency tree is an acyclic graph that maps connections between nodes and hence reconstructs a network.

Some properties of the Bayesian approach make it hard to apply to certain systems, such as biological systems. For example, the Bayesian approach assumes that an infinite number of models can explain the data, and only the probability of any given model being the correct model can be determined. Whereas one may simply accept the most probable model, in practice, data may be quite noisy and several very different models may have essentially the same ability to explain the data. Hence, a unique solution would not be found.

Bayesian networks, in principle, can handle continuous value variables, found for example in biological networks. However, in practice, data (i.e., mRNA levels) must be discretized to allow for the computation of joint probabilities between input variables. The optimal discretization method is not easily discernible and must balance more faithful representations of the input data (many fine bins) versus better estimations of joint probabilities (fewer large bins). Another problem may arise if feedback loops exist in the biological system, because the inferred Bayesian networks must be acyclic and hence cannot represent loops. In principle, this can be solved with dynamic Bayesian networks that can "unroll"

loops. However, in practice, the amount of data needed to pursue this approach is currently unfeasible. Indeed, current approaches have considerable trouble constraining static Bayesian networks, and the use of dynamic Bayesian networks for biological data has not been reported.

While some methods exist to reconstruct networks, these methods have some important limitations in the topologies of the networks that can be reconstructed, in the amount of and/or difficulty in collecting required data and in the uniqueness of the reconstructed solutions. Thus, it would be desirable to have techniques for reverse engineering arbitrary and/ or hidden networks, such as supply chain and biological networks, accurately and efficiently with data sets that can be reasonably collected.

SUMMARY OF THE INVENTION

The present invention provides techniques for reconstructing networks. In one aspect of the invention, a method for reconstructing a synthetic network, such as a synthetic biological network, comprises the following steps. Connections existing between nodes in the network are determined, on a node-by-node basis, by the following steps. An output of a node in the network is sequentially forced to a value of zero. A similarity measure is computed between the output of the node and an output of one or more other nodes in the network. One or more putative connections may be placed based on the similarity measure. A similarity value may be computed. The similarity value may be compared to a threshold value.

In another aspect of the invention, a method for reconstructing a supply chain network comprises the following steps. Connections existing between nodes in the network are determined, on a node-by-node basis, by the following steps. Perturbations in an output of a node in the network are monitored. A similarity measure is computed between the output of the node and an output of one or more other nodes in the network. One or more putative connections are placed based on the similarity measure.

A more complete understanding of the present invention, as well as further features and advantages of the present invention, will be obtained by reference to the following detailed description and drawings.

DETAILED DESCRIPTION OF PREFERRED EMBODIMENTS

Figure 1:
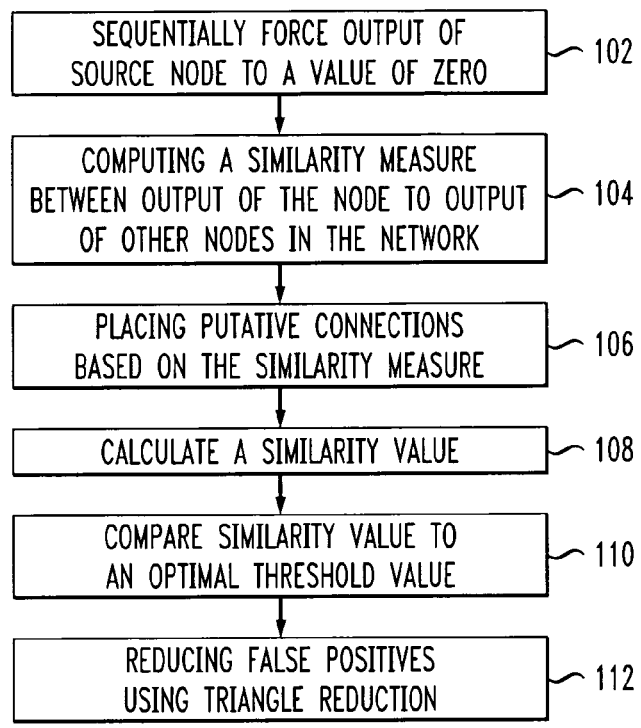
FIG. 1 is a flow chart illustrating an exemplary methodology for reconstructing a synthetic network according to an embodiment of the present invention.

FIG. 1 is a flow chart illustrating an exemplary methodology for reconstructing a synthetic network. The network may comprise one or more randomly generated connections. The techniques described herein are directed to reconstructions wherein qualitative connections are made. Synthetic networks may include networks comprising random placements of connections and synthetic biological networks comprising one or more connections representative of connections found in an organism, for example, connections found in the transcriptional regulatory network of *Escherichia coli*.

The reconstruction of the network may be conducted on a node-by-node basis. Each connection existing between any pairing of nodes may be determined. Thus, the techniques presented herein may be employed to conduct localized reconstructions of subsets of possible pairings of nodes in a network, as well as of an entire network.

A node-by-node determination is made of connections existing between nodes in the network. In step 102 of FIG. 1, the outputs of source nodes in the network are sequentially forced, i.e., node by node, to a value of zero. Forcing the output of a source node to a value of zero is referred to as "mutating," a term borrowed from the biological manipulation of inactivating single genes via genetic mutations. Alternatively, the mutated nodes could be forced up to the large value, an experimental manipulation referred to as "overexpression." This type of manipulation is often preferred experimentally, as it produces organisms that are more often viable as compared to "knock-outs," having zero output, that are not often viable. In the exemplary embodiment described herein, it was chosen to sequentially force the nodes to a value of zero, although very similar results could be obtained with "over-expression" manipulations as well.

In step 104 of FIG. 1, a similarity measure is computed between the output of the source nodes and the outputs of target nodes in the synthetic network. Qualitative information may then be deduced about the connections in the network. For example, it may be determined whether the connections exert a positive or a negative influence on the target nodes.

The error rate in the reconstruction of the synthetic network may be effected by factors such as noise, network size, number of connections and the Hill coefficients of the connections, as will be described in detail below. The network reconstruction, as presented herein, may be conducted with an error rate of less than or equal to about five percent, for example, with an error rate of less than or equal to about one percent. The determination of connections in a synthetic network will be described in detail below.

In step 106 of FIG. 1, putative connections are placed between the nodes based on the similarity measure. In step 108 of FIG. 1, a similarity value, i.e., a correlation value, may then be computed. In step 110 of FIG. 1, the similarity value may be compared to a threshold value. In step 112 of FIG. 1, false correlations, i.e., false positive correlations, may be reduced using triangle reduction, as will be described in detail below.

Figure 2:
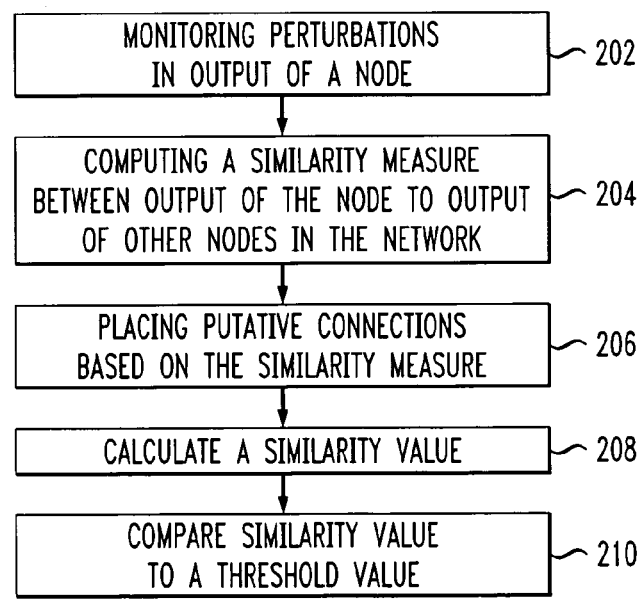
FIG. 2 is a flow chart illustrating an exemplary methodology for reconstructing a supply chain network according to an embodiment of the present invention.

FIG. 2 is a flow chart illustrating an exemplary methodology for reconstructing a supply chain network. The network may comprise one or more hidden connections. The term "hidden" refers to the fact that one or more of the connections existing in the network are unknown to the observer attempting the reconstruction.

A node-by-node determination is made of connections existing between nodes in the network. In step 202 of FIG. 2, perturbations in the output of a node, or nodes, in the supply chain network are monitored. In step 204 of FIG. 2, a similarity measure is calculated between the output of the node, or nodes, and the output of other nodes in the network. In step 206 of FIG. 2, putative connections are placed between the nodes based on the similarity measure. In step 208 of FIG. 2, a similarity value, i.e., a correlation value, may then be computed. In step 210 of FIG. 2, the similarity value may be compared to a threshold value. The determination of connections in a supply chain network will be described in detail below.

Figure 3:
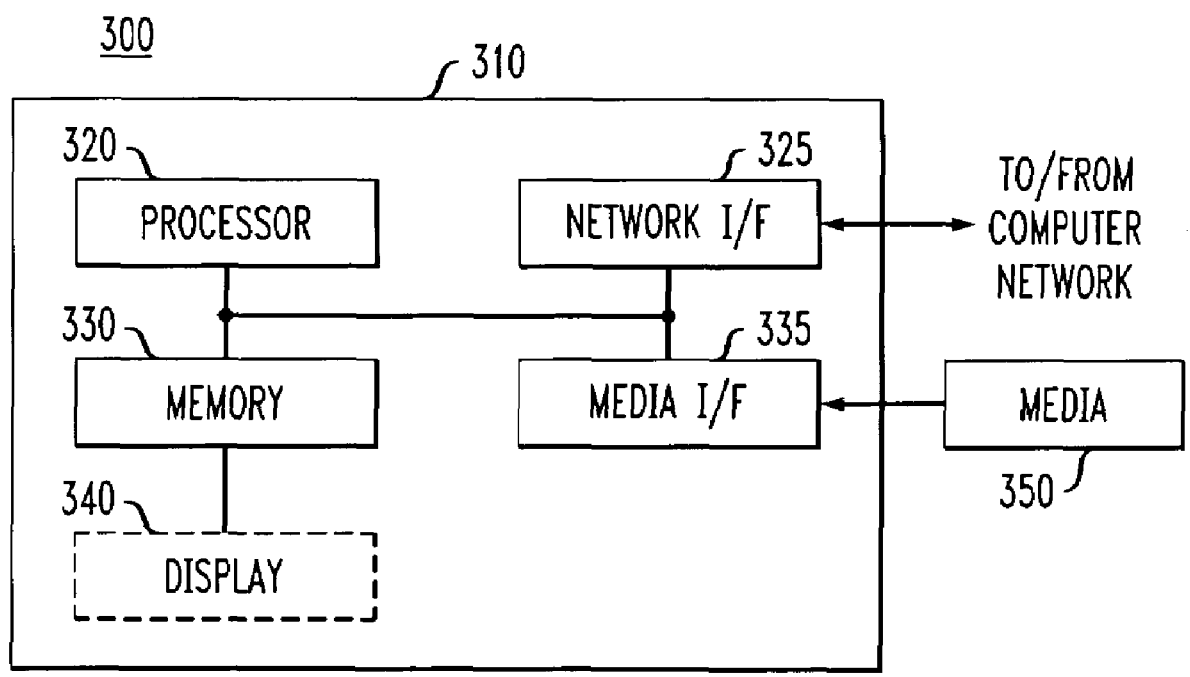
FIG. 3 is a block diagram of an exemplary hardware system suitable to implement one or more techniques of the present invention.

FIG. 3 is a block diagram of an exemplary system suitable to implement one or more of the present techniques. It is to be understood that apparatus 300 may implement the methodologies described above in conjunction with the description of FIG. 1 and FIG. 2. Apparatus 300 comprises a computer system 310 that interacts with media 350. Computer system 310 comprises a processor 320, a network interface 325, a memory 330, a media interface 335 and an optional display 340. Network interface 325 allows computer system 310 to connect to a network, while media interface 335 allows computer system 310 to interact with media 350, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer-system such as computer system 310, to carry out all or some of the steps to perform the methods or create the apparatus discussed herein. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 330 configures the processor 320 to implement the methods, steps, and functions disclosed herein. The memory 330 could be distributed or local and the processor 320 could be distributed or singular. The memory 330 could be implemented as an electrical, magnetic or optical memory, or any combination of these or other types of storage devices. Moreover, the term "memory" should be construed broadly enough to encompass any information able to be read from or written to an address in the addressable space accessed by processor 320. With this definition, information on a network, accessible through network interface 325, is still within memory 330 because the processor 320 can retrieve the information from the network. It should be noted that each distributed processor that makes up processor 320 generally contains its own addressable memory space. It should also be noted that some or all of computer system 310 can be incorporated into an application-specific or general-use integrated circuit.

Optional video display 340 is any type of video display suitable for interacting with a human user of apparatus 300. Generally, video display 340 is a computer monitor or other similar video display.

For ease of reference, the following description will be divided into the following, sections: (I) Network Construction, (II) Fully Synthetic Networks, (III) Semi-synthetic Networks, (IV) Simulation Protocol, (V) Data Processing, (VI) Effects of Added Noise on Reconstruction of Synthetic Networks, (VII) Effects of Network Properties on Reconstruction of Synthetic Networks, (VIII) Method to Reduce False Positives, (IX) Reconstruction of Transcriptional Control Network of *Escherichia coli*, (X) Study of Number of Data Points in Reconstruction, (XI) Study of Reproducibility, (XII) Supply Chain Networks, (XIII) Other Networks Suitable for Reconstruction.

I. Network Construction

The network comprises a network of N nodes labeled $u_i$ through $u_N$. The topology of the network is determined by one of a number of methods. The first method comprises a fully synthetic network wherein the topology of the connections is randomly determined, as is the nature of each of the connections. The second method comprises a semi-synthetic network. The topology of the connections in the semi-synthetic network is based on a real biological network, but the input-output functions of the nodes are synthetic functions, similar to those thought to exist, but not based on actual measurements. Fully synthetic and semi-synthetic networks are described in detail below.

II. Fully Synthetic Networks

The method comprises fully synthetic networks, namely a random assignment of connections using an approximate power law distribution thought to exist in many biological networks, see for example, H. Jeong et al., *The Large-Scale Organization of Metabolic Networks*, 407 NATURE 651-54

(2000). The outgoing degree of each node ($OD_i$ equals the number of outgoing connections from $u_i$) is determined using the following relationship:

$$r_i = OD_{min}^{-1.5} + (OD_{min}^{-1.5}) \cdot \text{rand}(0,1), \text{ wherein} \quad (1)$$

$$OD_i = \max(OD_{min}, \min(OD_{max}, r_i^{-2/3})) \quad (2)$$

and wherein $OD_{min}$ and $OD_{max}$ are the upper and lower bounds on the outgoing degrees allowed in the network and rand(0,1) is a uniformly distributed random number between zero and one. For each node, $OD_i$ connections are assigned to the N-1 other nodes without replacement. Hence, multiple outgoing edges from one node to a single target node are not considered. Likewise, outgoing connections leading from one node back onto itself (also referred to as autoregulation loops or self-loops) are not considered.

The governing system shown in Equation 3 below is adapted from M. K. Yeung et al., *Reverse Engineering Gene Networks: Integrating Genetic Perturbations With Dynamic Modeling*, 99 PROC. NATL. ACAD. SCI. USA 6163-68 (2002).

$$\frac{d}{dt}u_i = -\lambda u_i + \frac{a + \sum_{j \in A_i} u_j^{\gamma_{ij}}}{1 + \sum_{j \in A_i} u_j^{\gamma_{ij}} + \sum_{j \in R_i} u_j^{\beta_{ij}}} + \varepsilon_i. \quad (3)$$

For each node $u_i$, the output is assumed to decay with rate $\lambda$ that is set to unity for all simulations. The growth term $$\frac{a + \sum_{j \in A_i} u_j^{\gamma_{ij}}}{1 + \sum_{j \in A_i} u_j^{\gamma_{ij}} + \sum_{j \in R_i} u_j^{\beta_{ij}}},$$

describes the effects of inputs on the growth of node $u_i$. The growth term is composed of an $\alpha$ term that is fixed at 0.5 for all nodes. Excitatory and inhibitory inputs from other network nodes are incorporated via the $\gamma_{ij}$ and $\beta_{ij}$ terms, respectively. As described above, the number of outgoing connections from any node is set by Equation 2 above, but each connection is randomly assigned to be positive or negative. For simplicity, it is assumed that for any pair of input ($u_j$) and output ($u_i$) nodes, the connection is either excitatory ($\gamma_{ij}$ greater than zero), inhibitory ($\beta_{ij}$ greater than zero) or has no effect. Hence, in Equation 3 above, for any node ($u_i$), the sets $A_i$ and $R_i$ are disjoint. Because no node has auto-regulation, $\gamma_{ij}$ equals $\beta_{ij}$ which equals zero. Note that these terms are exponents that produce increasingly larger Hill coefficients with respect to the effect of an input node ($u_j$) on the time rate of change of the output node ($u_i$). Hence, all inputs are assumed to have equal "strength" although the "steepness" is modified by the magnitude of the $\gamma_{ij}$ and $\beta_{ij}$ terms. The last term, $\varepsilon_i$, is a Gaussian noise source that produces an independent random input to each node. While the noise sources are independent for each node, the magnitude is set to the same level for all nodes ($\text{var}(\varepsilon_i)$ equals $\varepsilon$).

III. Semi-synthetic Networks

So far, only random network reconstructions have been discussed. Recent studies, however, have suggested that real biological networks may have very different properties, with certain "motifs" or "modules" being over-represented in real networks, as compared to random networks. See, for example, S. S. Shen-Orr et al., *Network Motifs in the Transcriptional Regulation Network of Escherichia coli*, 31 NAT. GENET. 64-68 (2002) (hereinafter "Shen-Orr") and R. Milo et al., *Network Motifs: Simple Building Blocks of Complex Networks*, 298 SCIENCE, 824-27 (2002) (hereinafter "Milo"), the disclosures of which are incorporated by reference herein. To address the issue of reconstructing biological versus random networks, semi-synthetic networks, e.g., networks using the connection topology of the *Escherichia coli* transcription network adapted from the Shen-Orr study, were generated. This network contained 423 transcription factors and 578 interactions that embodied the sum of current knowledge of gene regulation of this model organism.

Constructing the *Escherichia coli* transcription network required starting with the interactions from the Shen-Orr study. Then, all autoregulation loops were removed. Removing all autoregulation loops reduced the number of interactions by 60 to 518. In the original data set, connections between transcription factors and promoters were positive, negative or both positive and negative. Connections in the third category, both positive and negative, were removed by randomly assigning these connections as either positive or negative. For the network, positive and negative connections were assigned non-zero values of $\gamma_{ij}$ and $\beta_{ij}$ terms, respectively, and the network was evolved using Equation 3.

IV. Simulation Protocol

The simulation protocol entailed repeatedly forcing a single node to a value of zero and then tracking the output of all nodes in the system. The node set to zero was termed the "mutant" node, as an analogous biological system can be envisioned in which a node is set to zero via experimental manipulation, i.e., knocking out a given gene. The data were collected by evolving the system of Equation 3 using Euler integration with a time step equal to 0.25 seconds. After sufficient time was given for the input conditions to decay, 20 samples were obtained for each node by collecting one sample time every 300 integration time steps. Note that the interval produced by 300 time steps is much larger than the characteristic time of the system. With this long spacing, and the addition of the $\varepsilon_i$ term, the samples were essentially independent and needed not be interpreted as time series data. Hence, for this case, the data can be considered as independent samples (i.e., ten normal and mutated samples) or a time series data (i.e., a temporal sequence of ten normal data points, followed by a temporal sequence of ten mutated data points). Moreover, the algorithm will process either type of data so that the interpretation is essentially unimportant.

Figure 4A:
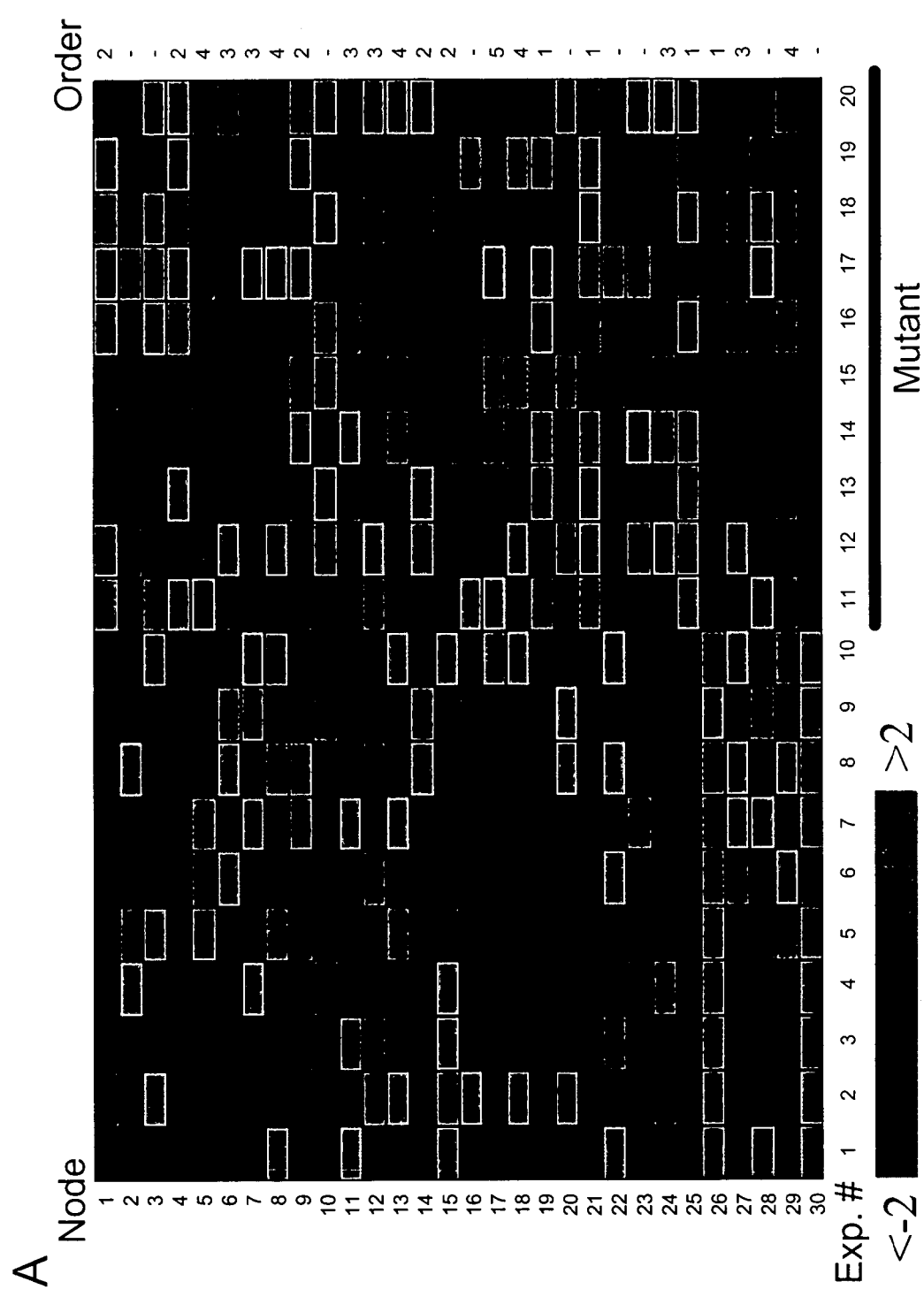
FIG. 4A is a diagram illustrating sample data from a 30 node synthetic network that is suitable for reconstruction according to an embodiment of the present invention.

FIG. 4A is a diagram illustrating sample data from a 30 node synthetic network that is suitable for reconstruction. In FIG. 4A sample data are shown for the 30-node network. The rows correspond to different nodes, and the columns correspond to different, experiments. The time data points are scaled to a zero mean with a unit variance across each row. The shaded gray scale shows the magnitude between −2 (black) and +2 (white). Rare data points larger in magnitude than this range exist and thus the scale key extends from less than −2 to greater than +2. The data shown are with node 30 (lowest row) as the mutant so that this node is assumed to be at its stable fixed point value (excluding slight variation for added noise) for the first ten experiments and then is forced to zero for the final ten experiments. The rows are labeled on the left by their number and on the right by the order of connection to node 30.

As shown by comparing columns, the response of the other nodes, i.e., nodes directly connected to the mutated node, often shows parallel behavior (as for Node 26 that has an activating input connection from node 30) or anti-parallel behavior (as for Node 25 that has a repressing input connection from node 30). The connections to both of these nodes are of order one as indicated on the right side of the figure. The order of these nodes corresponds to the minimum number of the connections needed to traverse from a source node to a destination node. Higher order connections also produce correlations.

Figure 4B:
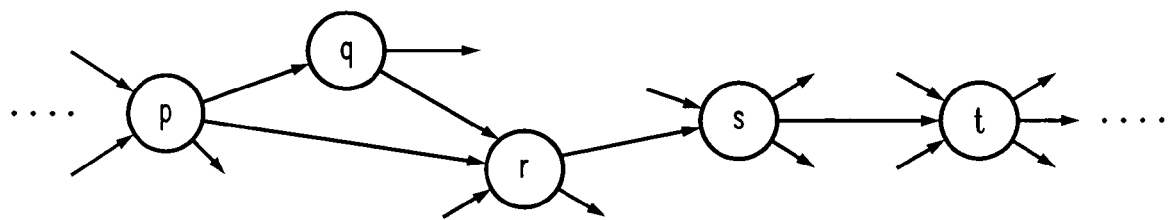
FIG. 4B is a diagram illustrating the concept of first order, second order and third order connections according to an embodiment of the present invention.

FIG. 4B is a diagram illustrating the concept of first order, second order and third order connections. For example, in FIG. 4B, some first order connections between nodes p and q and between nodes p and r are shown. Similarly, second order connections exist between nodes q and s and between nodes p and s. A third order connection exists between nodes p and t. The order is defined by the smallest number of arrows to go from the source to the destination, i.e., making node p to node r a first order, not second order, connection. For example referring to the diagram in FIG. 4A described above, nodes one and seven show a noticeable correlation although these nodes have connections of order two and three, respectively, to the mutated node.

V. Data Processing

When each node is mutated, the pairwise Pearson correlation coefficient ($\rho_{lm}$) between the perturbed node ($u_l$) and another node ($u_m$) is computed. Hence, a total of N-1 Pearson coefficients for each node are computed. As a simple baseline reconstruction algorithm, a threshold correlation value ($\rho_{thresh}$) is chosen. A putative connection (or edge) is then assumed from node $u_l$ to node $u_m$ when the pair-wise Pearson correlation coefficient exceeds the threshold ($|\rho_{lm}|$ greater than $\rho_{thresh}$). The sign of the correlation coefficient is then used give the edge a sign, i.e., plus being activating and minus being repressing.

Given that the underlying network that generated the data is known, reconstructed connections can be compared to the actual connections present in the network used to generate the data. A true positive corresponds to a correctly reconstructed connection with the correct sign, and a true negative corresponds to correctly determining that no connection is present. A false negative refers to a failure to correctly predict the existence of a connection or its correct sign. A false positive corresponds to a predicted connection that does not exist in the original network or has an incorrect assignment of the sign of the connection.

To investigate the accuracy of the method with respect to the threshold, the whole range of possible $\rho_{thresh}$ values from zero to one are investigated, with a step increment of 0.01, and receiver-operator characteristics (ROCs) are computed. In an ROC, a fractional error is plotted as the sum of normalized false positives and false negatives. The normalized false positives are computed as the number of false positives divided by the sum of false positives and true negatives. Likewise, the normalized false negatives are computed as the number of false negatives divided by the sum of true positives and false negatives. Herein, each ROC corresponds to the reconstruction of a single network. While a single network produces a noisy ROC trace, the results are well representative of results found when averaged over multiple networks. The reproducibility of the present methodologies across different production runs will be described in detail below.

VI. Effects of Added Noise on Reconstruction of Synthetic Networks

Figure 5:
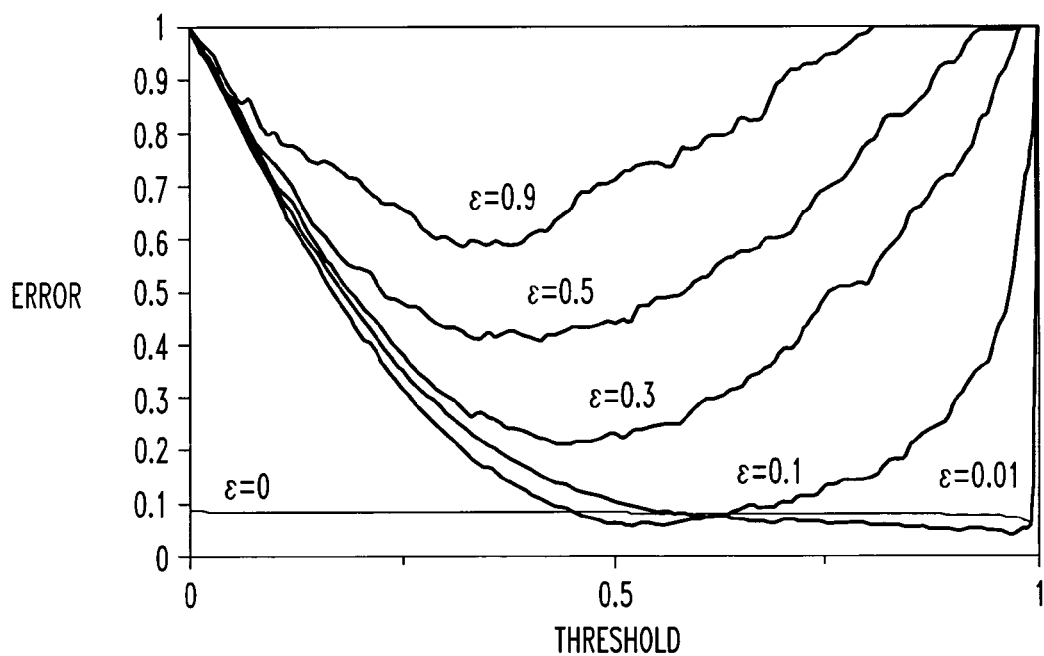
FIG. 5 is a graph illustrating the receiver-operator characteristics (ROCs) of a reconstructed network with variations in added noise according to an embodiment of the present invention.

FIG. 5 is a graph illustrating the ROCs of a reconstructed network with variations in added noise ϵ. In FIG. 5, fractional error is plotted as a function of $\rho_{thresh}$, the threshold used to decide whether or not to accept a given magnitude of correlation as a first order connection. The normalized error is computed as the sum of normalized false positives and normalized false negatives.

For a synthetic network, such as that presented in FIG. 5, network reconstruction may proceed with an error rate of less than or equal to about five percent, such as networks having a synthetic topology with properties that favor accurate reconstruction, such as sparse connections, low noise and/or close to linear input-output relationships for the nodes. Other networks may be reconstructed with an error rate of less than or equal to about one percent, such as networks similar to known biological networks that favor accurate reconstruction, such as very sparse connections, small input degrees and/or close to linear input-output relationships for the nodes in the network. An optimal threshold is chosen to balance the likelihood of producing a true positive with the likelihood of producing a true negative. Note that the goal is not necessarily the lowest total percent error, but instead, a threshold is chosen that substantially reduces false positives with a slight increase in false negatives.

Two main sources of error exist. False positives arise from correlations between nodes connected via one or more intermediate nodes, a situation found often in highly connected networks. False negatives occur when the correlation between two directly connected nodes is obscured by noise, non-linearity or multiple inputs to the target node.

In FIG. 5, the different traces show ROCs for increasing ϵ, the noise added to each node as the system is evolved. Otherwise, the network used to generate the data is unchanged. This network is fully synthetic, with 100 nodes having $OD_{min}$ and $OD_{max}$ set in Equations 1 and 2 to a value of one and five, respectively (mean outgoing order is 1.59). The trace labeled "ϵ=0" is essentially rectangular in shape, indicating that error shows little dependence on $\rho_{thresh}$. The minimum error is not zero due to false positives that result from high correlations with nodes having connections at orders of two or more.

With the addition of very small amounts of noise, e.g., ϵ equal to 0.01, false positives greatly increase for low values of $\rho_{thresh}$, but the minimum error remains below that found with no noise. With even more noise (ϵ equal to 0.1), the ROC is more U-shaped, as false negatives increase at higher $\rho_{thresh}$ values. As the noise levels increase further, the error rates generally increase over the whole range of $\rho_{thresh}$ values so that the U-shaped curves rise. The increase in error is predominantly caused by more false negatives at higher values of ϵ.

In contrast, false negatives show little change as shown by the fact that the right side of the ROC is still rectangular. Interestingly, the small amount of added noise lowers the minimum error below that found with no noise, a result that runs against intuition. A small amount of added noise lowering the minimum error below that found with noise is described in detail below in conjunction with the description of FIGS. 6A-C.

For the set of reconstructions shown in FIG. 5, the random network comprises 100 nodes with the output degree of the nodes set by Equations 1 and 2 above, with $OD_{min}$ equal to one and $OD_{max}$ equal to five. The network is unchanged except for the amplitudes of the independent noise sources being varied uniformly (var($\epsilon_i$) equals ϵ for all nodes in Equation 3 above).

Figure 6A:
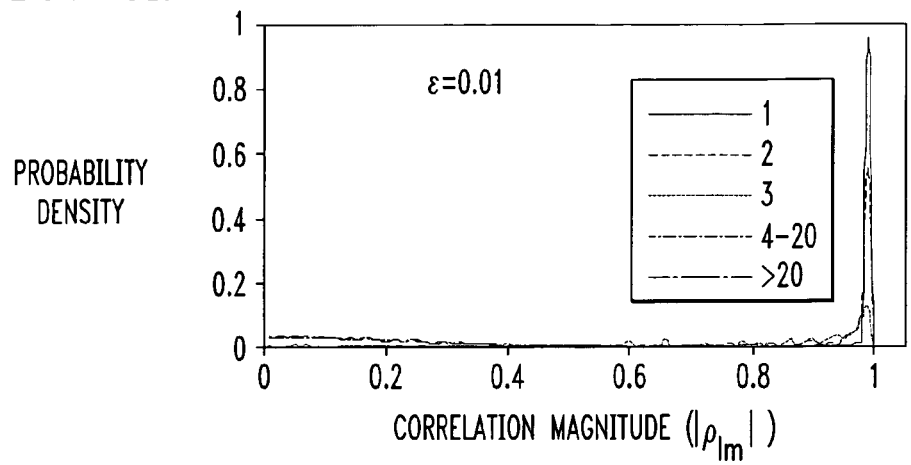
FIGS. 6A-C are graphs illustrating probability density functions (PDFs) for the magnitudes of correlation values according to an embodiment of the present invention.
Figure 6B:
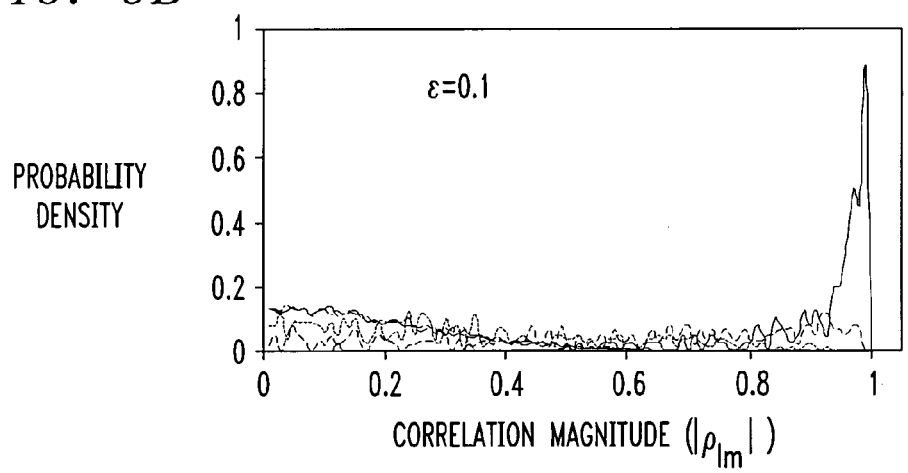
Figure 6C:
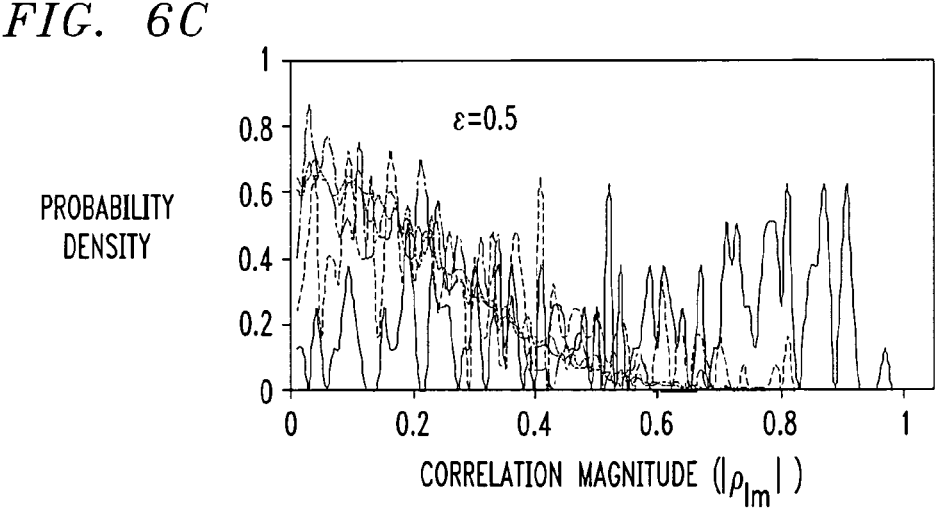

As was described above, a small amount of added noise can lower the minimum error, a result that runs against intuition. The noise can preferentially mask higher order connections that produce false positives while affecting the correlation of first order connections to a lesser extent. This point is explored further in FIGS. 6A-C described below. FIGS. 6A-C are graphs illustrating probability density functions (PDFs) for the magnitude of correlation values ($|\rho_{lm}|$). The different traces shown in FIGS. 6A-C indicate results for different orders of connection between the perturbed node ($u_l$) and the target node ($u_m$).

In FIGS. 6A-C, PDFs show the measured correlation as a function of the order of the connection. The actual connectivity of the network (which is the same network as described in conjunction with the description of FIG. 5 above) is used to compute the order of the connection between the perturbed node ($u_l$) and the target node ($u_m$). The PDF of the correlation magnitudes are shown as a function of the actual connection order. This manipulation is not possible if the original network is not known a priori, as such this is not a reconstruction technique. However, FIGS. 6A-C illustrate how the correlation method works.

FIGS. 6A-C show results for three levels of added noise, namely, $\epsilon$ equals 0.01, $\epsilon$ equals 0.1 and $\epsilon$ equals 0.5. The data correspond to the same noise levels as described above in conjunction with the description of FIG. 5. The traces show PDFs for different orders of connections as labeled, and as described below. The number of connections corresponding to the different traces are 159 at order one (trace labeled "1"), 248 at order two (trace labeled "2"), 345 at order three (trace labeled "3"), 5,332 for orders four through 20 (trace labeled "4-20") and 3,816 for the orders greater than 20 or disconnected (trace labeled ">20").

For very low noise, i.e., as in FIG. 6A, almost all of the first order connections generate high correlation magnitudes producing the tall spike in the first order trace (trace labeled "1"). As the order of the connections increases, the height of the peak near one decreases, and a smaller broader peak develops below 0.2 for the higher order connections (see the trace labeled "4-20" for orders four through 20 and the trace labeled ">20" for the orders greater than 20 which include no connections of any order).

Under these conditions, first order connections can easily be distinguished from very high order connections, but many connections of order two through four produce similar magnitudes of correlation and hence false positives. With slightly more noise, as shown for example in FIG. 6B, the peaks near one decrease, become blunt for order two connections and practically disappear for order three connections. Hence, first order connections produce correlation magnitudes near one, but higher order connection correlation magnitudes fall off quickly. With even more noise as shown in, i.e., FIG. 6C, the first order connections lose the peak near one, and the PDFs spread rightward so that measured correlations are more evenly distributed between zero and one, i.e., smeared. The measured correlations are now more or less equally likely for all values between zero and one. The first order connections become harder to distinguish on the basis of magnitude, and the resulting error rate increases markedly (as can be seen by reference to the trace labeled "$\epsilon$=0.5" in FIG. 5).

VII. Effects of Network Properties on Reconstruction of Synthetic Networks

In conjunction with the description of FIG. 5, it was established that $\epsilon$ equal to 0.1 produces a U-shaped ROC that is typical for higher levels of noise. This level of noise can also produce low error rates for $\rho_{thresh}$ at, or around, 0.5. For this level of noise, first order connections produce higher correlation magnitudes than higher order connections (see FIG. 6B). For this reason, $\epsilon$ equal to 0.1 was chosen for further study.

Figure 7A:
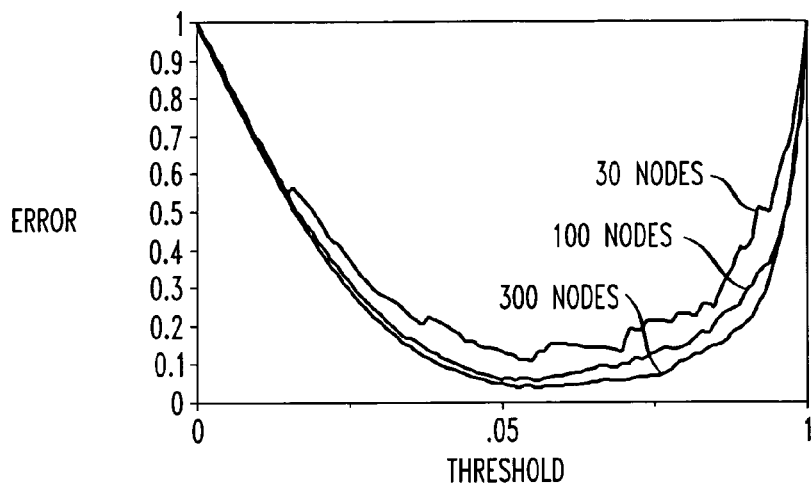
FIG. 7A is a graph illustrating the effects of the total number of nodes on the ROCs of a reconstructed network according to an embodiment of the present invention.

FIG. 7A is a graph illustrating the effects of the total number of nodes on the ROCs of a reconstructed network. Specifically, FIG. 7A shows sample ROCs for a reconstruction wherein the total number of nodes is set to 30, 100 or 300. The outgoing order of the nodes is fixed according to Equations 1 and 2 above, with $OD_{min}$ equal to one and $OD_{max}$ equal to five. For this set of reconstructions, the error rate increases as the number of nodes decreases. Namely, as the network size shrinks, the whole network becomes more connected and the number of higher order connections increases.

These higher order connections increase the number of false positives as correlations exist between nodes that are not directly connected. The number of higher order connections begins to decrease as network size increases, but the number of higher order connections does not completely go to zero. With the present method of generating random networks, every node has at least one outgoing connection. Hence, all nodes have at least one connection of order one, one connection of order two, and so on, as will be described in detail below in conjunction with the description of FIG. 9B.

Figure 7B:
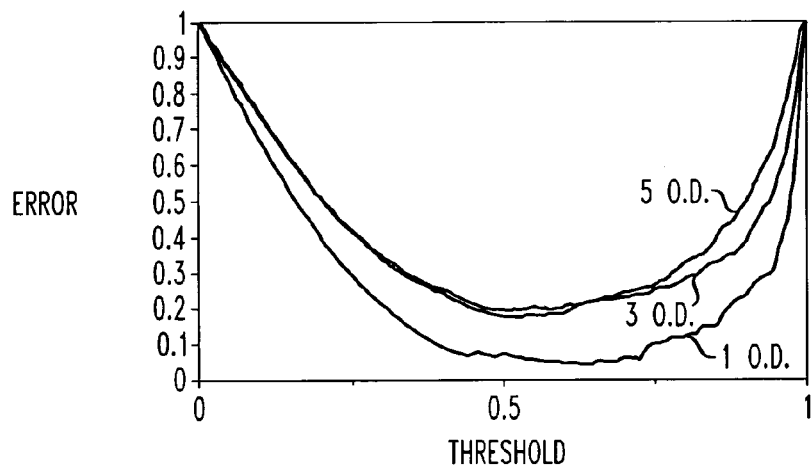
FIG. 7B is a graph illustrating the effects of outgoing connection degree on the ROCs of a reconstructed network according to an embodiment of the present invention.

FIG. 7B is a graph illustrating the effects of outgoing connection degree on the ROCs of a reconstructed network. The three traces shown in FIG. 7B indicate the results for outgoing degrees (O.D.) equal to one, three and five for every node in the network. Otherwise, the 100 networks have similar properties, and $\epsilon$ equals 0.1. The error rates increase as the outgoing degree increases due to the greater number of connections of orders greater than one. A second effect is that the number of completely disconnected pairs of nodes decreases. The disconnected pairs of nodes tend to have lower correlation $\rho_{lm}$ than those sharing a direct connection and those connections of an order just larger than one, i.e., two, three, etc. Given the lower correlation $\rho_{lm}$, the disconnected pairs of nodes are less likely to generate false positives. Therefore, sparse networks comprising many disconnected nodes tend to be reconstructed with lower error rates.

Figure 7C:
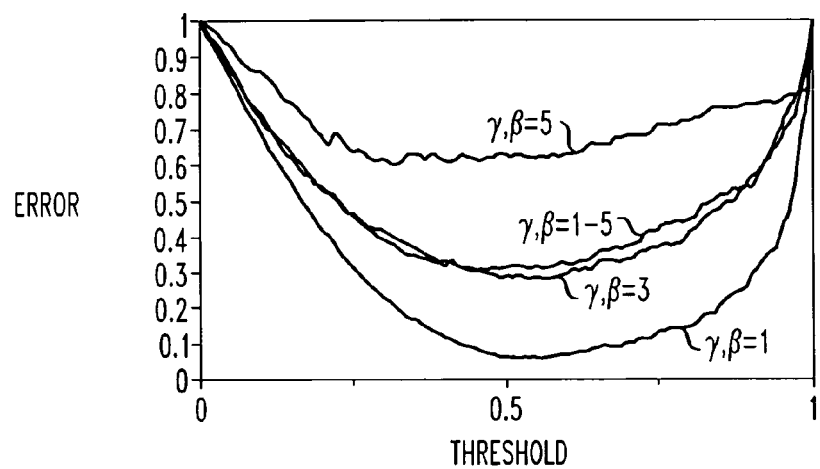
FIG. 7C is a graph illustrating the effects of variations in the Hill coefficient of cooperativity on the ROCs of a reconstructed network according to an embodiment of the present invention.

FIG. 7C is a graph illustrating the effects of variations in the Hill coefficients of cooperativity on the ROCs of a reconstructed network. Namely, FIG. 7C shows the effects of varying $\gamma$ and $\beta$, the exponents on the inputs to each node in Equation 3 above. Recall that the $\gamma$ and $\beta$ exponents set the Hill coefficients on the inputs to the nodes. The values of $\gamma$ and $\beta$ may be one, three, five or uniformly distributed over the range one through five, as indicated by the labels on the traces. For this set of reconstructions, the topology of the connections is preserved, but the exponents are changed. The best reconstruction occurs when all exponents are one so that the input-output relations are almost linear. Exponents of magnitude one, shown labeled as "$\gamma,\beta=1$" in FIG. 7C, produce a predominately linear input-output relationship over a large range of input levels. Exponents of a higher magnitude produce a steeper and less linear response that is less well detected by the correlation method, although other similarity measurements could produce better results. Hence, the ROCs show increasingly higher error rates when the exponent magnitudes are all set to three and five, shown labeled as "$\gamma,\beta=3$" and "$\gamma,\beta=5$," respectively.

Another case is shown in which the exponent magnitudes are uniformly distributed between one and five, labeled as "$\gamma,\beta=1$-$5$" in FIG. 7C. Unlike the other runs, the network in this case is heterogeneous with respect to both the output order and the connection exponents. The ROC for this heterogeneous network with the mean exponent equal to three is quite similar to the ROC for an instance wherein all exponents are set to three, i.e., compare trace labeled "$\gamma,\beta=1$-$5$" with trace labeled "$\gamma,\beta=3$"). Hence, there appears to be little effect of homogenous versus heterogeneous networks, at least for the present case wherein exponents are varied.

VIII. Method to Reduce False Positives

The results so far demonstrate that low error rates are achieved when the correlation magnitudes of order one connections are larger than that of higher order connections and unconnected nodes. However, as was shown in FIGS. 6A and 6B, order one connections cannot always be easily distinguished from order two through four connections on the basis of correlation alone, and therefore a number of false positives seems unavoidable. To improve the ability to reconstruct networks, two strategies may be employed. First, attempts are made to choose an optimal threshold value ($\rho_{optimal}$) to distinguish first order connections from other order connections. Second, attempts are made to reject false positives that are a likely result of second order connections masquerading as first order connections. These two strategies are discussed in more detail below.

Figure 8:
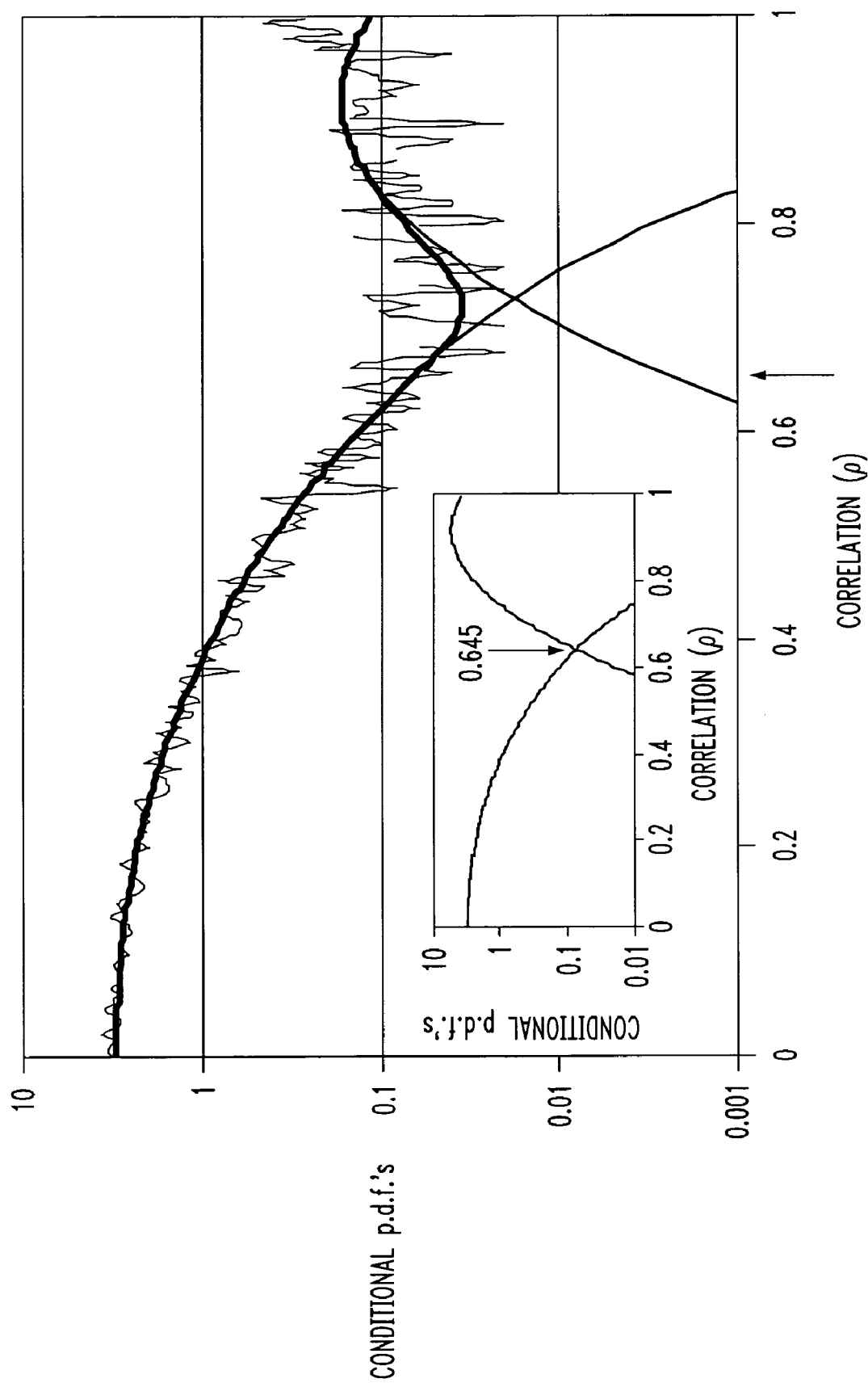
FIG. 8 is a histogram illustrating a distribution of correlation magnitude values according to an embodiment of the present invention.

FIG. 8 is a histogram illustrating a distribution of correlation magnitude values. To choose an optimal threshold value, the logarithm of correlation magnitudes is plotted. The jagged thin line represents the actual histogram of correlation magnitudes. The randomness reflects both the added noise and the noise inherent to a randomly constructed network of finite size. The histogram is fit by $P_{fit}$ ($\rho$, k, f, $\sigma$) (see Equation 4 below) as indicated by the thicker smooth line. The fit shows two peaks that follow two separate components. The first component is a ratio of gamma functions that fits the distribution predicted for the correlation of two random vectors of dimension k. With the logarithmic axis, this component produces the half parabola shown by the thin line on the left side of FIG. 8. The second component is a Gaussian distribution that is fit to the peak in the histogram produced by first order connections in the network. The two separate components are combined into a single fit using a weighting factor f for the first term and (1-f) for the second term. The full fitting function may be represented as:

$$P_{fit}(\rho, k, f, \sigma) = \frac{f}{\Omega_0(k)}(1-\rho^2)^{\frac{k-3}{2}} + (1-f)G(\rho, \mu, \sigma), \quad (4)$$

wherein f is the weighing factor, k is the number of degrees of freedom, $\mu$ is the mean of the Gaussian distribution and $\sigma$ is the variance of the Gaussian distribution.

The parameters space of f, k, $\mu$ and $\sigma$ is exhaustively scanned over reasonable parameter ranges for the optimal set that minimizes the root mean square (RMS) error between the histogram and the $P_{fit}$ ($\rho$, k, f, $\sigma$) over the range of zero less than $\rho$ less than one. Note that k corresponds to the dimensions of two random vectors in the ratio for gamma functions. It might be predicted that k should be 20 to correspond to the correlations over 20 independent data points. Hence, k would correspond to the pair-wise correlation predicted for two independent and disconnected nodes. However the empirically determined k producing the best fit is generally less. As was highlighted above, the first peak in the histogram of FIG. 8 corresponds to all nodes that are not directly connected and further that second, third and other higher order connections may produce some correlation. Another reason k will be less than 20 is that the mutated data set is not truly random, as the final ten data points are all equal to zero.

The fit to the histogram in FIG. 8 is used to choose the optimal $\rho_{optimal}$ as follows. Without the weighing factor f the first term is assumed to equal the probability density function for a measured correlation magnitude ($\rho$) conditioned on the existence of no first order connection between the nodes, as true negative (TN), as shown in Equation 5 below.

$$\Pr(\rho \mid TN) = \frac{1}{\Omega_0(k)}(1-\rho^2)^{\frac{k-3}{2}} \quad (5)$$

Without the (1-f), the term $$\frac{1}{\Omega_0(k)}(1-\rho^2)^{\frac{k-3}{2}}$$

is assumed to equal the probability density function for a measured correlation magnitude ($\rho$) conditioned on the existence of a first order connection, a true positive (TP), as shown in Equation 6 below.

$$Pr(\rho|TP)=G(\rho,\mu,\sigma) \quad (6)$$

In the present method, $\rho_{optimal}$ is chosen such that $\Pr(\rho|TN)$ equals $\Pr(\rho|TP)$ for $\rho$ equal to $\rho_{optimal}$.

In FIG. 8, the inset shows two traces, $\Pr(\rho|TN)$ on the left and $\Pr(\rho|TP)$ on right, the components of the fitting function without the contributions of the weighting factor terms. The left component is $\Pr(\rho|TN)$, the conditional probability of a correlation magnitude given the pair of nodes is not connected (a true negative). The right component is $\Pr(\rho|TP)$, the conditional probability of a correlation magnitude given the pair of nodes is connected (a true positive). The intersection point at $\rho_{optimal}$ 0.645, is chosen as the best $\rho_{thresh}$ that just balances competing effects, namely a smaller $\rho_{thresh}$ increases false positives and a larger $\rho_{thresh}$ increases false negatives. The optimal point does not need to correspond to the minimum in the histogram in FIG. 8. The arrow in the figure shows the corresponding point that is to the left of the minimum in the histogram. The difference results from the influence of the weighting factor f that is not included in calculating $\rho_{optimal}$ but is included in the fit to the histogram.

The second strategy to improve reconstructions is to attempt to reduce false positives by looking for second order connections that can explain high correlations between two nodes. Such a strategy is undertaken because second order connections can show a high correlation that gives the appearance of first order connections. Such a situation may be illustrated by reference back to FIG. 4B, described above. As shown schematically in FIG. 4B, nodes q and s have a second order connection with node r as an intermediate. If the measured correlation between nodes q and s is high enough, the reconstruction method will predict a false first order connection between these nodes. Such a scenario can happen often. For example, in FIGS. 6A and 6B, also described above, many connections of order two produce correlation magnitudes as large as would direct connections, i.e., first order connections. For an additional specific case, see FIG. 4A, described above, wherein node 15 exhibits a relatively high correlation with node 30, although these nodes are connected via a second order connection.

In the present method, triangle reduction is used to reduce false positives by removing a reconstructed first order connection if a second order connection exists with sufficient correlation. The existence of such a second order connection is investigated by looking at all N-2 possible second order paths using the method described below. Using FIG. 4B as an example, one may assume the correlation between node q to node s exceeds the threshold, i.e., $|\rho_{qs}|$ is greater than $\rho_{thresh}$, such that a putative first order connection is reconstructed from node q to node s. For this example, there are real first order connections between q and r, and between r and s.

When all Pearson correlation coefficients are calculated, the magnitudes of the correlations between q and r and between r and s must exceed that of the direct connection $|\rho_{qs}|$, e.g., $\min(|\rho_{qr}|,|\rho_{rs}|)$ greater than $|\rho_{qs}|$. Next, the signs of the correlation must agree so that $\text{sign}(\rho_{qr}\cdot\rho_{rs})$ equals sign $(\rho_{qs})$. This condition assures that a putative first order connection is replaced by a second order connection of a similar net positive or negative sign. With both of these conditions satisfied, the putative first order connection is removed. The strategy is to try to remove false positive connections if an alternative explanation can be found based on a second order connection. This process can also, however, generate false negatives. For example, a true positive could be wrongly removed from node p to node r if the second order path through node q shows higher correlations.

The two strategies outlined above can, in principle, be applied separately or sequentially. To apply the strategies sequentially, the optimal threshold is first found by using the fit to the histogram in FIG. 8. Next, putative first order connections are determined for this threshold value. The method above is then applied to remove false positives. As shown in Table 1 below, the number of false positives may be reduced for the reconstructed networks, for example those described in conjunction with the description of FIG. 5 and FIGS. 7A-C. The number of false positives may be reduced for the reconstructed network that will be described in detail below in conjunction with the description of FIG. 9A. For each network reconstruction, the optimum threshold is provided with the number of true positives and true negatives, and false positives and false negatives, both before and after (labeled "Pre/Post" in Table 1 below) the application of the triangle reduction.

IX. Reconstruction of Transcriptional Control Network of *Escherichia coli*

So far, only random networks have been reconstructed. Recent studies have suggested that real biological networks may have unique properties, with certain "motifs" or "modules" being over-represented as compared to random networks. See Shen-Orr and Milo. To address the issue of reconstructing biological versus random networks, a network was generated using the connection topology of the *Escherichia coli* transcription network adapted from Shen-Orr.

Figure 9A:
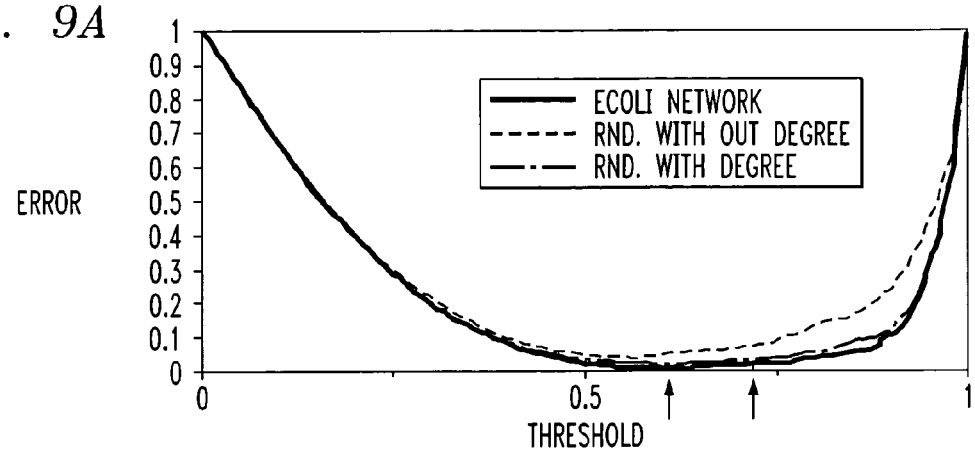
FIG. 9A is a graph illustrating the ROCs for a reconstructed *Escherichia coli* network according to an embodiment of the present invention.

FIG. 9A is a graph illustrating the ROCs for a reconstructed *Escherichia coli* network. The results for the reconstructed *Escherichia coli* network are shown as the trace labeled "*E. coli* Network" in FIG. 9A. The minimum error is 0.011 which occurs at $\rho_{thresh}$ equal to 0.62 (shown by the left arrow below the abscissa). This value of $\rho_{thresh}$ produces 929 false positives, a number that far exceeds the 518 actual connections in the network. However, the error rate is low as the number of false positives are normalized by the sum of the number of false positives and true negatives (number of true negatives equals 177,059). Such a high number of true negatives can arise for large and sparse networks as the number of potential connections is N(N-1).

For this example, the 518 true connections cover less than 0.3 percent of the 178,506 possible connections in the network. This example clearly illustrates the need for the method of choosing $\rho_{optimal}$ to reduce false positives. As shown in Table 1 above, the number of false negatives is reduced to 212 by choosing $\rho_{thresh}$ equal to $\rho_{optimal}$ equal to 0.72 (shown by the right arrow below the abscissa). With the application of triangle reduction, false positives are further reduced to 85. In both cases, false positives are decreased at the expense of increasing overall error. Such an approach may be justified as fewer false positives may be preferred to fewer false negatives. With application to real biological systems, the confirmation of putative connections will require further experimentation with other techniques. An excessive number of false positives may provide too many false leads to be feasibly rejected with other experimental techniques.

TABLE 1

| FIG. | $\rho_{optimum}$ | Error Pre/Post | TP Pre/Post | FP Pre/Post | TN Pre/Post | FN Pre/Post | Network Parameters |
|---|---|---|---|---|---|---|---|
| 5 | 0.69 | 0.0637/ 0.0136 | 159/ 157 | 621/ 10 | 9120/ 9731 | 0/ 2 | $\epsilon = 0.01, \gamma, \beta = 1$, Nodes = 100 |
| 5, 7A, 7C | 0.68 | 0.0916/ 0.0767 | 147/ 147 | 157/ 12 | 9584/ 9729 | 12/ 12 | $\epsilon = 0.1, \gamma, \beta = 1$, Nodes = 100 |
| 5 | 0.59 | 0.4946/ 0.5107 | 82/ 79 | 101/ 74 | 9640/ 9667 | 77/ 80 | $\epsilon = 0.5, \gamma, \beta = 1$, Nodes = 100 |
| 7A | 0.64 | 0.1437/ 0.1078 | 34/ 34 | 32/ 2 | 800/ 830 | 4/ 4 | $\epsilon = 0.1, \gamma, \beta = 1$, Nodes = 30 |
| 7A | 0.68 | 0.0579/ 0.0555 | 421/ 420 | 546/ 130 | 88710/ 89126 | 23/ 24 | $\epsilon = 0.1, \alpha, \beta = 1$, Nodes = 300 |
| 7B | 0.66 | 0.0489/ 0.0423 | 96/ 96 | 87/ 23 | 9713/ 9777 | 4/ 4 | O.D. = 1, $\epsilon = 0.1$, Nodes = 100 |
| 7B | 0.65 | 0.2134/ 0.1825 | 248/ 246 | 385/ 24 | 9215/ 9576 | 52/ 54 | O.D. = 3, $\epsilon = 0.1$, Nodes = 100 |
| 7B | 0.68 | 0.2267/ 0.2263 | 402/ 388 | 289/ 22 | 9111/ 9378 | 98/ 112 | O.D. = 5, $\epsilon = 0.1$, Nodes = 100 |
| 7C | 0.63 | 0.3042/ 0.2836 | 115/ 115 | 268/ 67 | 9473/ 9674 | 44/ 44 | $\gamma, \beta = 3, \epsilon = 0.1$, Nodes = 100 |
| 7C | 0.65 | 0.6573/ 0.6488 | 57/ 57 | 154/ 67 | 9587/ 9670 | 102/ 102 | $\gamma, \beta = 5, \epsilon = 0.1$, Nodes = 100 |
| 7C | 0.67 | 0.3640/ 0.3456 | 106/ 105 | 299/ 58 | 9442/ 9683 | 53/ 54 | $\gamma, \beta = 1–5, \epsilon = 0.1$, Nodes = 100 |
| 9A | 0.72 | 0.0205/ 0.0449 | 508/ 495 | 212/ 85 | 177776/ 177903 | 10/ 23 | $\gamma, \beta = 1, \epsilon = 0.1$, Nodes = 423 |

The reconstruction of the *Escherichia coli* network is then compared to the reconstruction of a random network of similar size. The first random network is constructed with $OD_{min}$ equal to one and $OD_{max}$ equal to three to produce an average outgoing degree of 1.1891, as compared to 1.2246 for the original *Escherichia coli* network. As shown by the trace labeled "rnd. without degree" in FIG. 9A, the error rate is much higher for this network as compared to the *Escherichia coli* network.

Figure 9B:
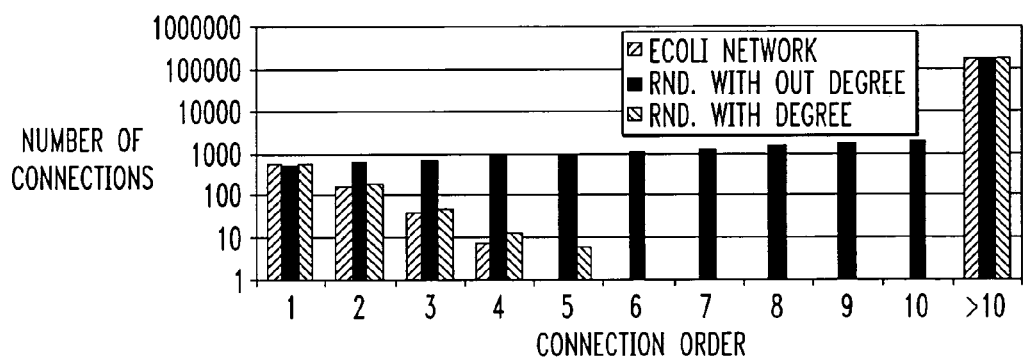
FIG. 9B is a histogram illustrating a number of various order connections of the reconstructed *Escherichia coli* network and of similar size random networks according to an embodiment of the present invention.
Figure 9C:
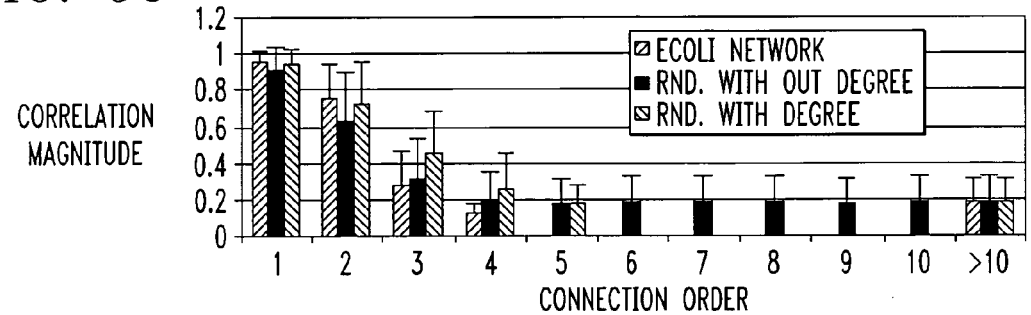
FIG. 9C is a histogram illustrating the mean correlation produced by different order connections according to an embodiment of the present invention.

Two factors increase the error rate. First, the error rate will rise as a result of an increase in the number of connections of an order greater than one, as shown by the solid bars (labeled "rnd. with out degree") in FIG. 9B. FIG. 9B is a histogram illustrating a number of various order connections of the reconstructed *Escherichia coli* network and of similar size random networks. These higher order connections, especially the order two and three connections, produce correlations similar to a first order connection, and as such increase false positives, see FIG. 9C. FIG. 9C is a histogram illustrating the mean correlation produced by different order connections. As was described above in conjunction with the description of FIGS. 6A-C, these higher order connections can produce correlation magnitudes that are just as high as direct connections, and hence produce false positives.

Figure 9D:
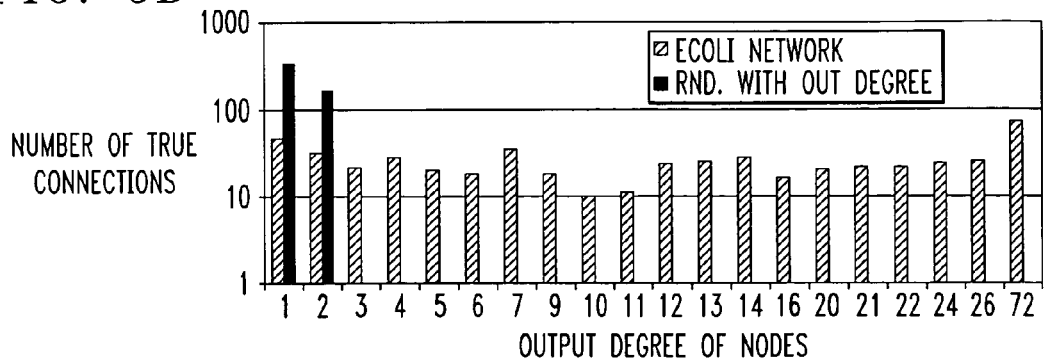
FIG. 9D is a histogram illustrating a distribution of connections with respect to the output degree of a source node according to an embodiment of the present invention.

To understand why the random network has so many more high order connections, consider FIG. 9D. FIG. 9D is a histogram illustrating a distribution of connections with respect to the output degree of a source node. The *Escherichia coli* network, shown as hatched bars (labeled "*E. coli* network") shows a large number of connections arising from a few nodes with high output degrees. For example, the two right most hatched bars correspond to nodes with output degrees of 26 and 72, respectively.

In contrast, the random network, shown as solid bars (labeled "rnd. without degree" in FIG. 9D) consists of nodes with output degrees of one and two only. Given that each node has at least one outgoing connection, every node is then connected to at least one other node by an order one connection, to at least one other node by an order two connection and to at least one other by an order three connection, and so on. In contrast, the *Escherichia coli* network can be considered more star-like with a few nodes having a high output degree and many nodes having an input degree of one. The term "star-like" indicates that there are a few highly connected nodes that output to many nodes having single inputs. Hence, there are not many long range connections that can produce false positives. Moreover, many nodes have an output degree of zero. As a result, there tends to be fewer long-range connections. Indeed, no two nodes are connected in the present network by more than three sequential connections.

A second source of error is an increase in the input order of nodes in the random network. The *Escherichia coli* network has relatively few nodes with a high output degree and many nodes with an input degree of one. The nodes of the *Escherichia coli* network are the easiest to reconstruct, as the correlation tends to be highest when the receiving node has a single input. For example, when the target node has an input degree of one, the mean correlation magnitude is 0.971 (standard deviation equals 0.0292) in the *Escherichia coli* network and 0.960 (standard deviation equals 0.0458) in the random network.

In contrast, as the number of input nodes increases, each input contributes less to the overall output, and hence, the measured correlation decreases. For example, when the target node has an input degree of two, the mean correlation magnitude is 0.961 (standard deviation equals 0.0546) in the *Escherichia coli* network and 0.908 (standard deviation equals 0.126) in the random network. Given these statistics, it is expected that direct connections to input degree one nodes would be correctly identified more readily than direct connections to input degree two nodes. For the examples shown, the *Escherichia coli* network has 228 connections to nodes of input degree one and 142 connections to the less accurately reconstructed nodes of input degree two. For comparison, the random network has 157 connections to nodes input degree one and 186 connections to the less accurately reconstructed nodes of input degree two.

To check that the incoming degree of reconstructed nodes has an important effect on the error, another random network was developed wherein the input and output degrees of each node were preserved as the internode connections were rearranged. With this manipulation, the randomized network was reconstructed with approximately the same error level as that of the original *Escherichia coli* network (compare the solid trace labeled "*E. coli* network" and the line/dash trace labeled "rnd. with degree" in FIG. 9A). The small differences in the two traces are attributable to random variations. Similar degree-preserving random networks produced results virtually identical to the *Escherichia coli* results. The profile of the connection orders is similar but not identical to the order-preserving random network and original *Escherichia coli* network (compare hatched bars labeled "*E. coli* network" and hatched bars labeled "rnd. with degree" in FIG. 9B).

Therefore, preserving input and output degree of nodes does necessarily preserve the orders of the connections between any pair of nodes. Given that the degree-preserving network is reconstructed in a similar fashion to the original network, it may be concluded that the distribution of input and output degrees of nodes plays an important role in the ability of the method to reconstruct networks. It is important to note that all three networks just considered may also be considered sparse by computing the ratio of connections to nodes. The present method may be used to reconstruct synthetic networks using an analysis with the Pearson correlation coefficient. The method has favorable properties including the ability to reconstruct networks with a wide range of sizes (tens to hundreds of nodes), connectivities, and noise levels anticipated to be appropriate for the properties of gene regulatory networks found in biological systems. The method has been shown to work on both random networks and those based on biological topologies and on networks with dense or sparse connections. In fact, the sparsest networks are reconstructed with the lowest error rates, a feature that bodes well for the reconstruction of real biological networks, as real biological networks are reported by many researchers to be sparse. See for example, M. K. Yeung et al., *Reverse Engineering Gene Networks Using Singular Value Decomposition and Robust Regression,* 99 PROC. NATL. ACAD. SCI., 6163-68 (2002), H. Jeong et al., *The Large-Scale Organization of Metabolic Networks,* 407 NATURE 651-54 (2000) and H. Jeong et al., *Lethality and Centrality in Protein Networks,* 411 NATURE 41-42 (2001).

Besides sparseness, the *Escherichia coli* regulation network is found to have other properties that help in accurate reconstruction by the present methods. The *Escherichia coli* regulation network is fairly star-like with a small number of nodes having a high output degree, i.e., many nodes having an input degree of one. This feature improves the reconstruction as correlations are strongest when few connection impinge on the target node.

Other improvements in performance may be produced through other methods of detecting correlation signals. For example, mutual information may be considered for more non-linear systems although more data may be required. Also consider that, as a source node is mutated, the resulting signal at a connected node shows a resulting jump in level (see FIG. 4A). An alternative analysis method could thus be based on finding nodes that show a step in output in response to the mutation of a source node. In this alternative method, correlation is detected by a measured step instead of the Pearson based correlation method employed above. If the measurements are taken sequentially to produce a time series, then detecting steps in output may be enhanced by computing the derivative of the time signal. The optimal correlation method for any given system may require some combination of the above-mentioned present approaches.

X. Study of Number of Data Points in Reconstruction

The number of data points used in the study deserves consideration. The runs without noise could have been accomplished with one point under each the normal and the mutated condition, for a total of two data points per node versus 20 data points per node as shown in FIG. 4A. With no noise, the extra data points are redundant. Namely, the same value will be repeated ten times with no gain in information over a single point. Ten points were chosen as a reasonable estimate of what might be collected experimentally when some amount of noise in unavoidable. As shown below, more data can be collected to improve reconstruction accuracy to some degree.

Figure 10A:
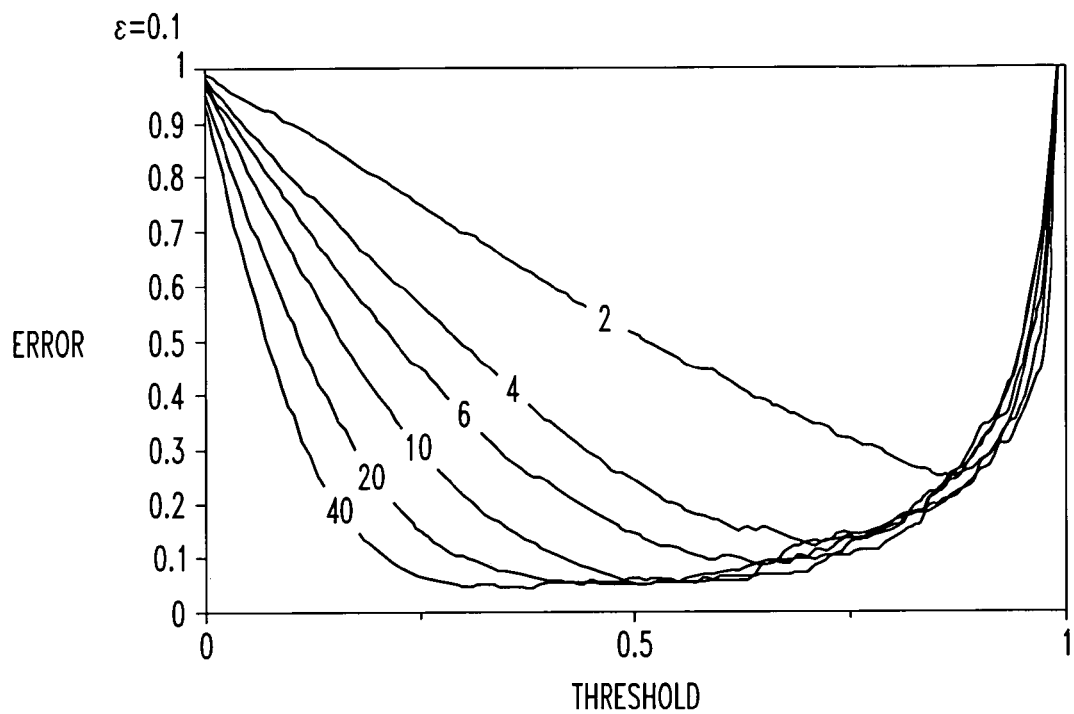
FIGS. 10A-B are graphs illustrating reconstruction accuracy as a function of the number of nodes present according to an embodiment of the present invention.
Figure 10B:
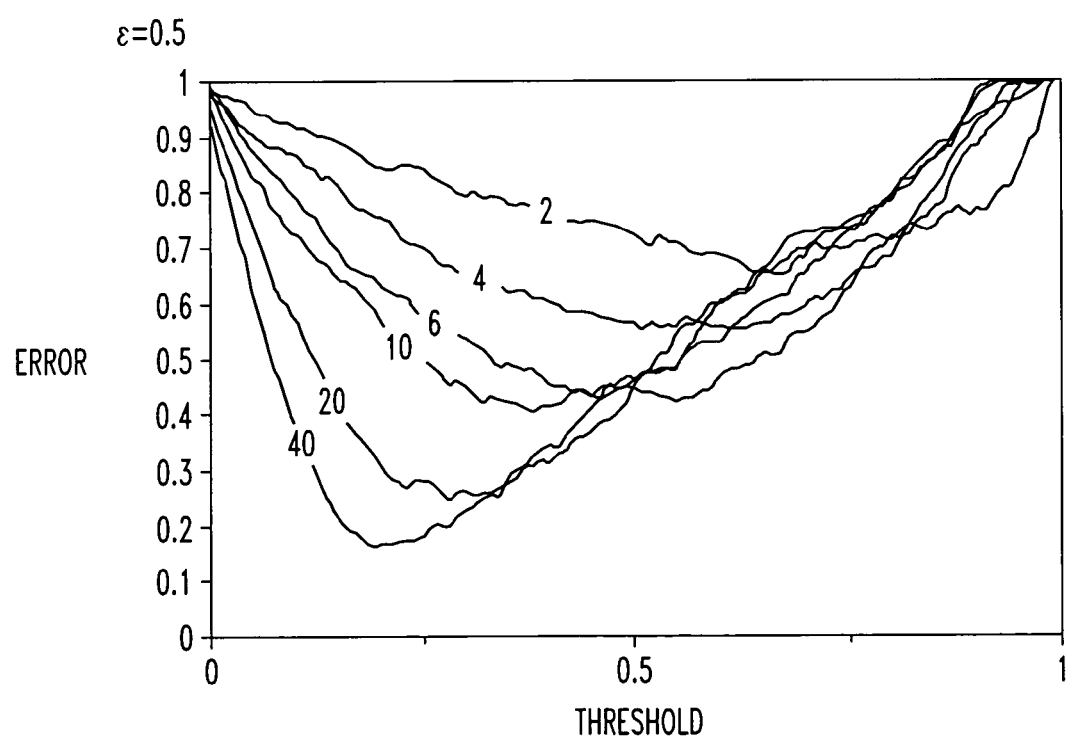

A number of runs were conducted to address the issue of reconstruction accuracy versus the number of points. FIGS. 10A-B are graphs illustrating reconstruction accuracy as a function of the number of nodes present. Specifically, FIG. 10A shows results for the same network as described in conjunction with the description of FIG. 5 above, with the same noise level ($\epsilon$ equal to 0.1). The traces show results for two, four, six, ten, 20 and 40 points for both the normal and the mutant case (total points equal to four, 12, 20, 40 and 80, respectively). With regard to FIG. 4A, the normal case comprises the first points collected on the left hand side. The mutant case comprise the points collected on the right hand side. The minimum number of points possible is one normal and one mutant point, but this case is degenerative as all nodes are 100 percent correlated if any noise is added to the signal.

The results show that as the number of points decrease, the error rate increases. Specifically, the false positives show the greatest change as more points produce a lower falling phase for low $\rho$ and corresponding increase in the width of the basin. Note that the basin widens but the minimum does not change very much. This result can be anticipated because the error rate does not go to zero without added noise. Instead the higher order connections produce false positives.

Intuitively, more points should decrease the effects of added noise approximating the rectangular case found with $\epsilon$ equal to zero, as described in conjunction with the description of FIG. 5 above. However the results are slightly more complicated. For example, FIG. 10B shows results for $\epsilon$ equal to 0.5, a higher level of noise that markedly degrades reconstruction performance (see the description of FIG. 5 above). With this higher level of added noise, reconstruction is poor for a small numbers of points, e.g., see the two and four point traces in FIG. 10B). As the number of points increases, the accuracy improves, although the improvement is predominately focused on decreasing false positives that produce a leftward basin near $\rho$ equal to 0.2. Hence, more points do not compensate for the increased false negatives at higher $\rho$ when the added noise level is large.

As shown above, the accuracy of reconstruction can be increased by collecting more data. However, the cost of collecting experimental data will likely limit the actual number of points collected. In most of the reconstructions shown, twenty samples were collected (ten control and ten mutated) to reconstruct each node, for a total of 20×N samples for the whole network. If each sample corresponds to a given gene chip, that samples' N gene expression levels, then the network reconstruction requires a total of $20 \times N^2$ gene expression levels to be measured.

The current cost of data collection will require a balance of cost (fewer points) versus accuracy (more points). While the method as described herein is simple and straight forward, deviations in parts of the method can be envisioned that use the collected data more effectively, so that fewer total points are required. For example, in the current method, new data is collected to reconstruct each node. However, the data collected for one node could potentially be reused for other nodes, i.e., any measured correlation between nodes could be considered evidence for a connection. Alternatively, multiple nodes could be mutated at once if there was some evidence that these nodes had disjoint sets of neighbors in the network.

XI. Study of Reproducibility

Figure 11A:
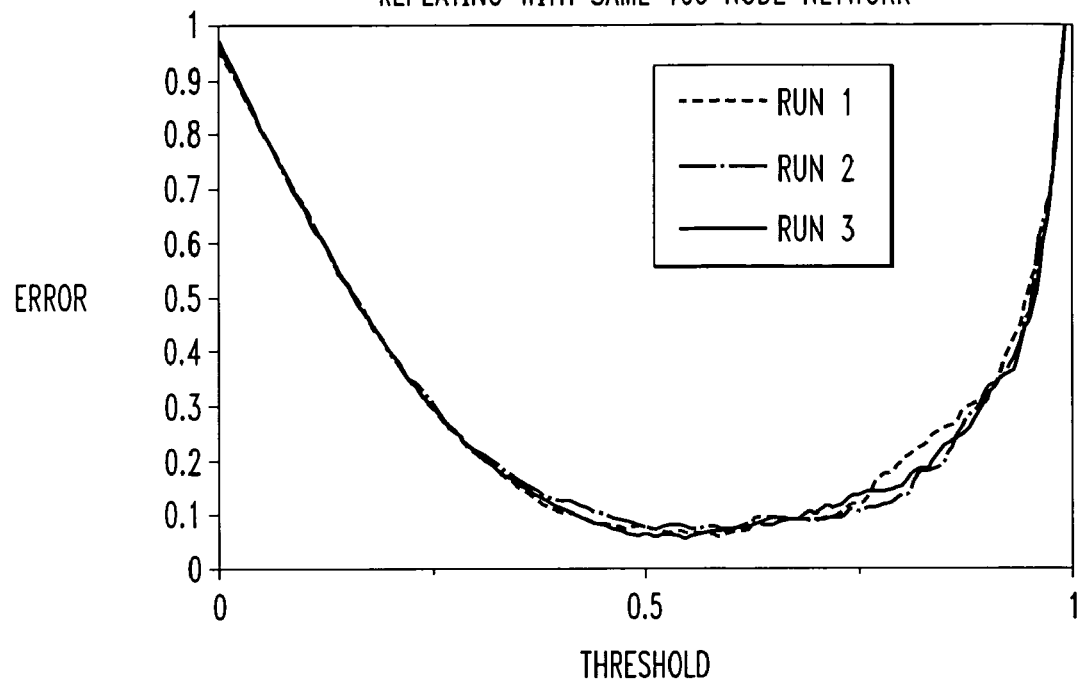
FIGS. 11A-B are graphs illustrating reproducibility of the present techniques using different network reconstruction runs according to an embodiment of the present invention.
Figure 11B:
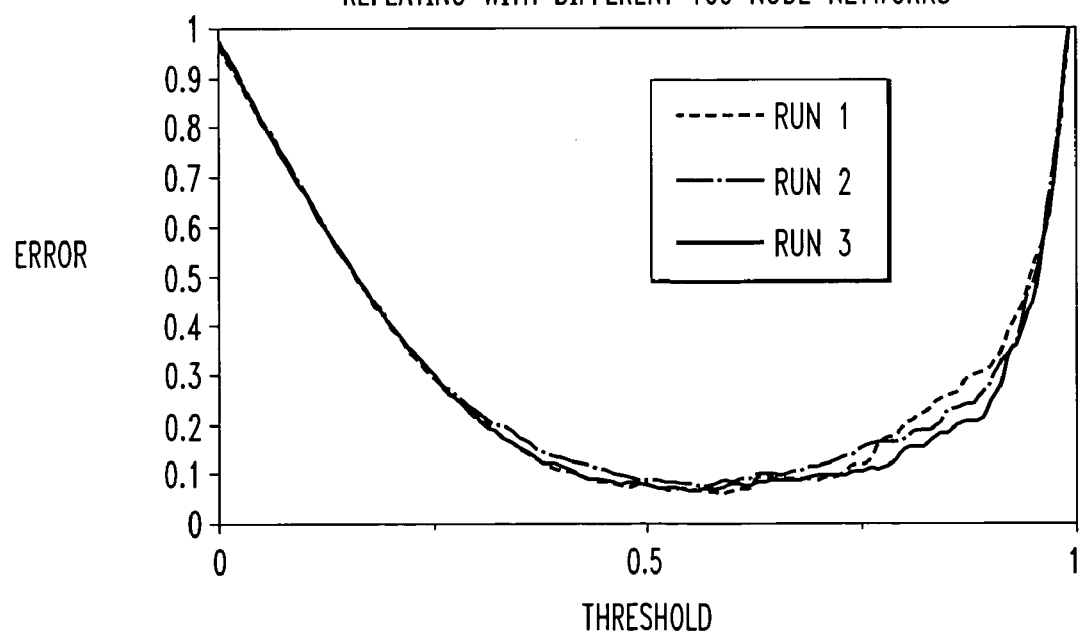

So far, the results have been presented for a single reconstruction of a network of any given type. An issue may arise as to the generality of such findings, i.e., would results differ substantially across reconstructions with different random noise inputs, or different random topologies. Another set of runs addressed the issue of reproducibility with different reconstruction runs. FIGS. 11A-B are graphs illustrating reproducibility of the present techniques using different network reconstruction runs. Specifically, FIG. 11A shows results for the same network as that described in conjunction with the description of FIG. 5 with the same noise level ($\epsilon$ equals 0.1). The traces show results for three separate runs where the generated data is different as a result of the added noise term. The results show little variation from run to run. FIG. 11B shows results for the same network as that described in conjunction with the description of FIG. 5 with the same noise level ($\epsilon$ equals 0.1) labeled as "Run 1," as in FIG. 11B. The other two traces, labeled "Run 2" and "Run 3," show results for two other runs with different 100 node network nodes with the output degree of the nodes being set by Equations 1 and 2 above, i.e., with $OD_{min}$ equal to one and $OD_{max}$ equal to five. Again, the results show little variation with each run. Taken together the result from FIG. 11A and FIG. 11B show little variation across runs, with or without changing network geometry. The results are reproducible and should not differ substantially across reconstruction runs or similar-sized networks with different random topologies.

XII. Supply Chain Networks

The present techniques may be used to reconstruct any network in which the output of nodes can be determined over time or under different conditions. One must also be able to measure perturbations in the nodes (or ideally to force a perturbation directly) to find which other nodes are connected to the perturbed node. Suitable networks include supply chain networks.

Figure 12:
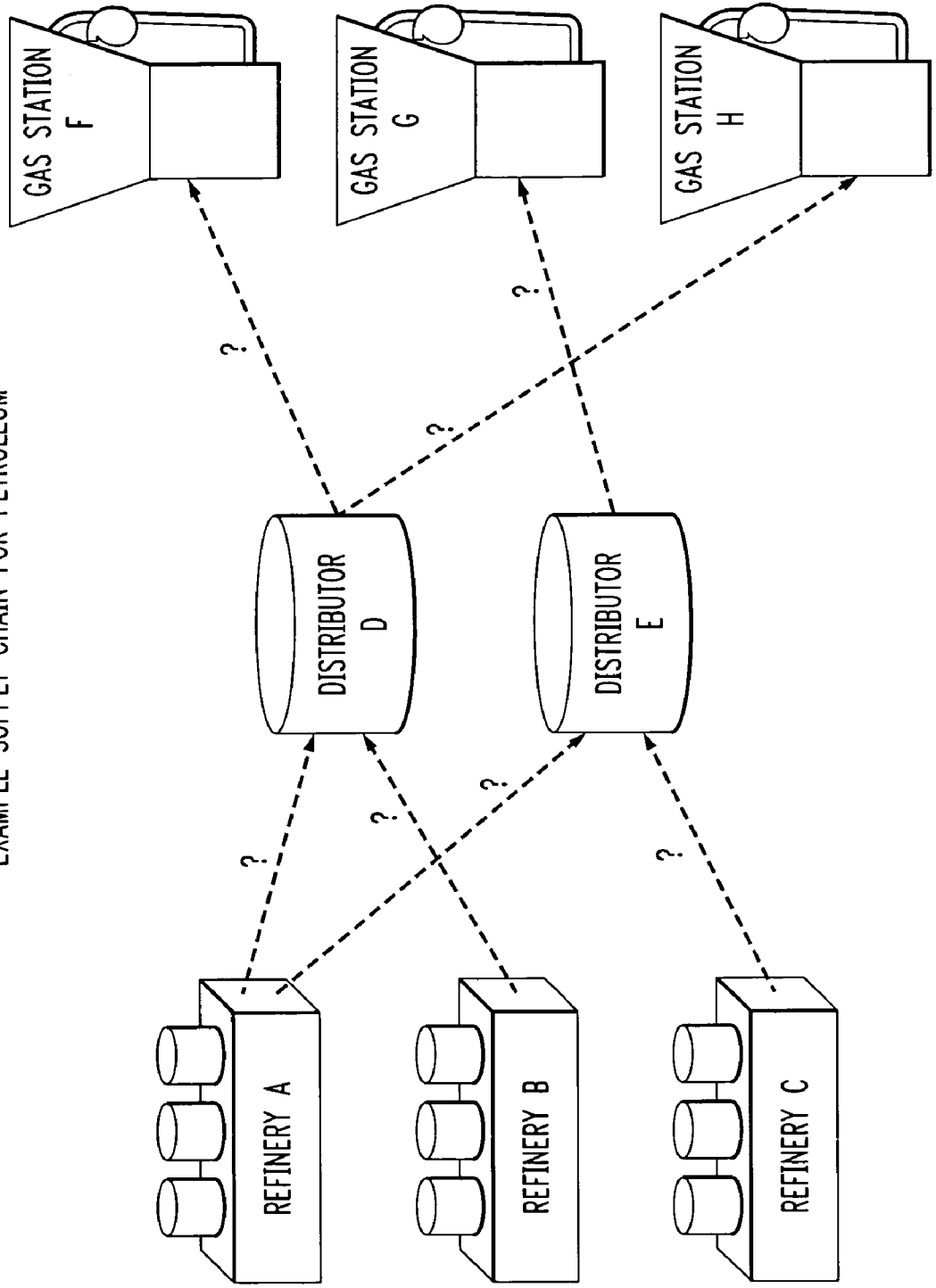
FIG. 12 is a diagram illustrating an exemplary supply chain for petroleum distribution.

Such supply chain networks can be reconstructed by looking for correlations between the supply (or price) of building materials, e.g., raw materials and subcomponents, and the supply (or price) of finished materials. An exemplary supply chain network may comprise a petroleum distribution network. FIG. 12 is a diagram illustrating an exemplary supply chain network for petroleum distribution. In FIG. 12 three refineries (A, B and C) are shown that supply two distributors (D and E). The distributors in turn supply three gas stations (F, G and H). One may desire to determine the supply chain from the refinery to the gas station. FIG. 12 includes dashed arrows with question marks to illustrate potential connections within the supply chain.

Figure 13:
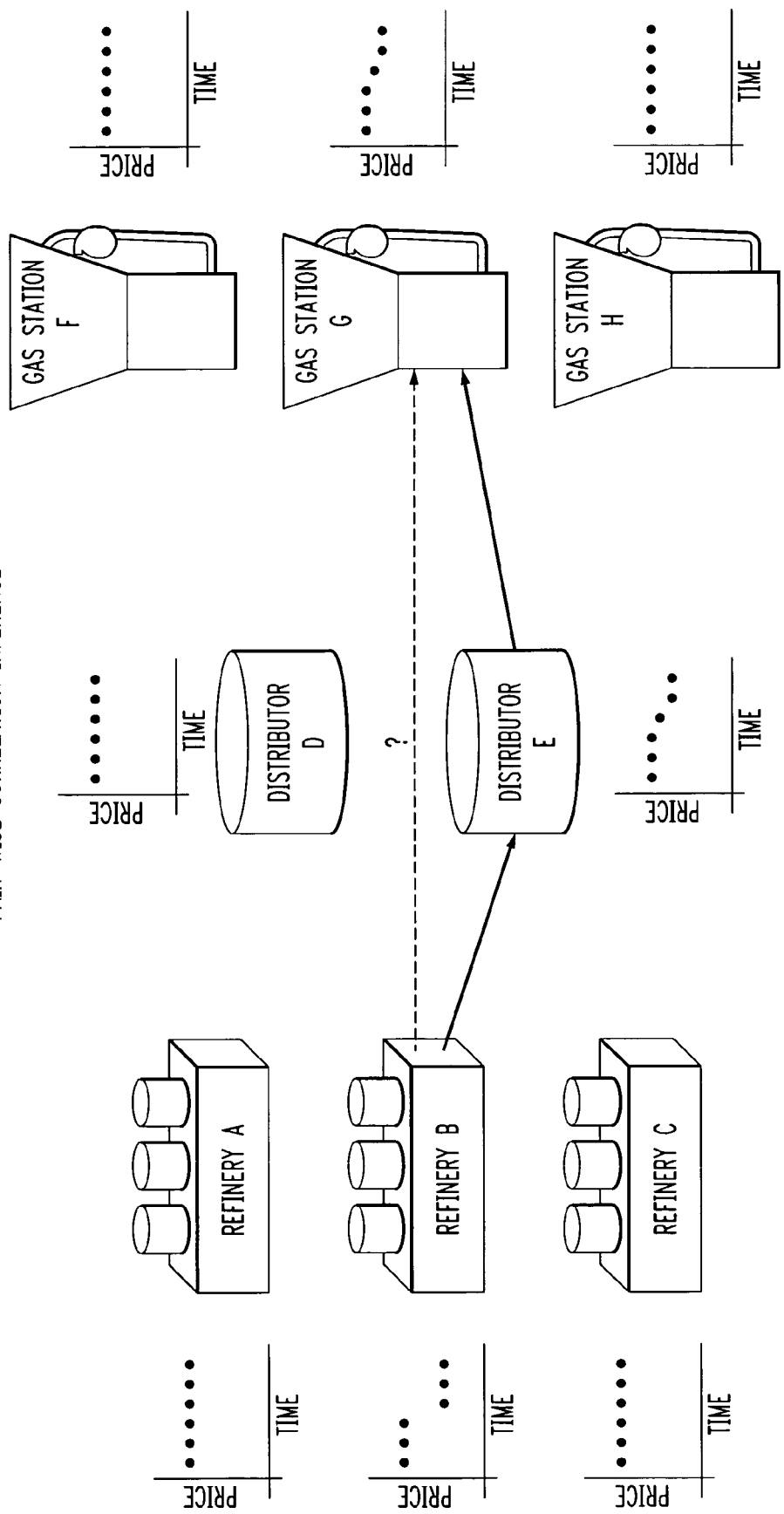
FIG. 13 is a diagram illustrating the reconstruction of an exemplary supply chain for petroleum distribution according to an embodiment of the present invention.

Assuming that the actual supply chain is unknown, pairwise correlation analysis may be used to reconstruct the supply chain network. FIG. 13 is a diagram illustrating the reconstruction of an exemplary supply chain for petroleum. Assume that a single point is perturbed by direct manipulation or via other external fluctuation. For example, in FIG. 13, the cost of gas from Refinery B is assumed to decrease in a step-like fashion, as indicated by the graph next to Refinery B, while the price of gas from the other refineries remains constant. The price of gas from the other network components may be observed to look for correlations that exist. The price of gas from Distributor E shows similar price behavior, therefore the computed correlation, i.e., Pearson, mutual information or similar measure, between the two price signals will be large. According to the present methods, a threshold may be chosen and a putative connection will be placed if the calculated correlation is larger than this threshold. For the example shown in FIG. 13, an arrow is draw from Refinery B to Distributor E.

Typically, correlations would be computed between all pairs of nodes to look for any correlations that are larger than the threshold, and a putative connection placed. For almost all cases in the example shown in FIG. 13, there is very little change in the price with time. As such, correlations will be low and no arrow will be placed. For example, no arrow would be placed to Refinery A, Distributor D or Gas Station F.

A complication, however, occurs for the case of Refinery B to Gas Station G wherein the signal will also be correlated but to a lesser degree than that between Refinery B and Distributor E. In this case, as described above, a putative connection may be placed if the correlation is greater than the set threshold. If the putative connection is made, the connection would be incorrect because typically gas stations do not buy directly from refineries. One solution to prevent this error is to incorporate a priori knowledge in the form of node labels and associated rules. For example, a rule might comprise the fact that Refinery nodes cannot directly connect to Gas Station nodes.

If such a priori knowledge is not known, one can still use other general network properties. For many networks, the connections are sparse meaning that only a small percentage of possible pair-wise connections exist. For this case, the triangle reduction rule can be applied. In the case shown in FIG. 13, assume strong correlations are found from Refinery B to Distributor E and from Distributor E to Gas Station G, then the hypothesis of a direct connection of Refinery B to Gas Station G is rejected based on the assumption that the indirect path via Distributor E is a more likely explanation for the measured correlation. This is only one way in which assumptions of general network properties can be used to improve inferences of unknown network even without more specific, direct a priori rules about node connectivity.

XIII. Other Networks Suitable for Reconstruction

Suitable networks for reconstruction include the following non-exhaustive list of networks. Correlations between stock trades could be used to predict networks of insider traders. Correlations between currency trades could reveal the hidden networks between money dealers. These networks may be fluid and changing. However, even a partial reconstruction of a given point in time could prove useful to a government or financial organization. Correlations of e-mail messages (perhaps even for binary encoded messages) could be used to predict, for example, social networks and communicating groups of terrorists. If contraband or illegal narcotics could be perturbed, for example, by treatment with chemical markers, distribution networks could potentially be uncovered.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method for reconstructing a synthetic network, the method comprising the steps of:
   determining, on a node-by-node basis, connections existing between nodes in the network by the steps of:
   sequentially forcing an output of a node in the network to a value of zero;
   computing a similarity measure between the output of the node and an output of one or more other nodes in the network; and
   placing one or more putative connections based on the similarity measure.

2. The method of claim 1, wherein the network comprises a synthetic biological network.

3. The method of claim 1, wherein at least one of the connections comprises a local connection.

4. The method of claim 1, wherein the network comprises at least one source node and at least one target node.

5. The method of claim 4, wherein the at least one source node exerts a positive influence on the at least one target node.

6. The method of claim 4, wherein the at least one source node exerts a negative influence on the at least one target node.

7. The method of claim 1, wherein the network comprises at least one randomly generated connection.

8. The method of claim 1, wherein the network comprises all randomly generated connections.

9. The method of claim 1, wherein the network comprises at least one connection representative of one or more connections found in a transcriptional regulatory network of *Escherichia coli*.

10. The method of claim 1, wherein sequentially forcing the output of the node in the network to a value of zero comprises experimental manipulation.

11. The method of claim 1, wherein sequentially forcing the output of the node in the network to a value of zero comprises manipulating a gene.

12. The method of claim 1, wherein each of the nodes in the network comprises at least one outgoing connection.

13. The method of claim 1, wherein the placing step further comprises the steps of:
   computing a similarity value; and
   comparing the similarity value to a threshold value.

14. The method of claim 13, wherein the threshold value comprises an optimal threshold value.

15. The method of claim 13, wherein the threshold value balances true positives with true negatives.

16. The method of claim 13, wherein the threshold value balances false positives with false negatives.

17. The method of claim 13, wherein the similarity value comprises a correlation value.

18. The method of claim 13, wherein the similarity value is less than the threshold value indicating that no connection between the nodes exists.

19. The method of claim 13, wherein the similarity value comprises a Pearson correlation coefficient.

20. The method of claim 13, wherein the similarity value is calculated for a plurality of possible pairings of nodes in the network.

21. The method of claim 13, wherein the similarity value is calculated for a subset of possible pairings of nodes in the network.

22. The method of claim 1, wherein each of the connections comprises an order corresponding to a minimum number of individual connections needed to traverse from the node to the one or more other nodes.

23. The method of claim 22, wherein the order is used to reduce false correlations.

24. The method of claim 23, wherein the false correlations comprise false positive correlations.

25. The method of claim 23, wherein the false correlations comprise false negative correlations.

26. The method of claim 23, wherein false correlations are reduced using triangle reduction.

27. The method of claim 22, wherein the order is used to reduce false correlations by distinguishing first order connections from all other order connections.

28. An apparatus for reconstructing a synthetic network, the apparatus comprising:
    a memory; and
    at least one processor operative to:
    determine, on a node-by-node basis, connections existing between nodes in the network by the steps of:
       sequentially forcing an output of a node in the network to a value of zero;
       computing a similarity measure between the output of the node and an output of one or more other nodes in the network; and
       placing one or more putative connections based on the similarity measure.

29. An article of manufacture for reconstructing a synthetic network, comprising:
    a computer-readable medium having computer-readable code embodied thereon, the computer-readable code comprising:
    a step to determine, on a node-by-node basis, connections existing between nodes in the network by the steps of:
       sequentially forcing an output of a node in the network to a value of zero;
       computing a similarity measure between the output of the node and an output of one or more other nodes in the network; and
       placing one or more putative connections based on the similarity measure.

* * * * *